United States Patent [19]
Bonini et al.

[11] Patent Number: 5,679,541
[45] Date of Patent: Oct. 21, 1997

[54] PROGRAMMED CELL DEATH ANTAGONIST PROTEIN

[75] Inventors: Nancy M. Bonini, Pasadena; Seymour Benzer, San Marino, both of Calif.; William M. Leiserson, North Haven, Conn.

[73] Assignee: California Institute of Technology, Pasadena, Calif.

[21] Appl. No.: 195,152

[22] Filed: Feb. 14, 1994

[51] Int. Cl.⁶ .............................. C12P 21/06; C12N 5/00; C12N 15/00; C07H 19/00
[52] U.S. Cl. .................. 435/69.1; 435/240.2; 435/252.3; 435/320.1; 530/300; 530/350; 536/22.1; 536/23.1; 536/23.5; 536/24.3; 536/24.31
[58] Field of Search ...................... 435/69.1, 240.2, 435/320.1, 252.3; 530/300, 350; 536/22.1, 23.1, 23.5, 24.3, 24.31

[56] References Cited

U.S. PATENT DOCUMENTS 5,360,893  11/1994  Owens et al. ........................... 530/350

OTHER PUBLICATIONS

Hengartner, M.O., et al., "Caenorhabditis elegans gene ced–9 protects cells from programmed cell death", *Nature*, vol. 356: 494–499 (1992).

Williams, G.T., et al., "Molecular Regulation of Apoptosis: Genetic Controls on Cell Death", *Cell*, vol. 77: 777–779 (1993).

Ma, C., et al., "The segment Polarity Gene hedgehog is Required for Progression of the Morphogenetic Furrow in the Developing Drosophila Eye", *Cell*, vol. 75: 927–938 (1993).

Heberlein, U., et al., "The TGFβ Homolog dpp and the segment Polarity Gene hedgehog Are Required for Propagation of a Morphogenetic Wave in teh *Drosophila Retina*", *Cell*, vol. 75: 913–926 (1993).

Miura, M., et al., "Induction of Apoptosis in Fibroblasts by IL–1β–Converting Enzyme, a Mammalian Homolog of the C. elegans Cell Death Gene Ced–3", *Cell*, vol. 75: 653–660 (1993).

Buckler, A.J., et al., "A Novel Gene Containing a Trinucleotide Repeat That Is Expanded and Unstrable on Huntington's Disease Chromosomes", *Cell*, vol. 72: 971–983 (1993).

Ellis, H.M., et al., "Genetic Control of Programmed Cell Death in the Nomatode C. elegans", *Cell*, vol. 44: 817–829 (1986).

Abrams et al., "Programmed cell death during *Drosophila* embryogenesis," Development, 117: 1, pp. 29–43 (1993).

Randazzo et al., "Rescue and regulation of proboscipedia a homeotic gene of the antennapedia complex," Development, 113:1 pp.257–272 (1991).

Glover "Principles of DNA Cloning", Gene Cloning pp. 1–20 (1984).

Current Protocols in Molecular Biology, *Screening of Recombinant DNA Libraries*, Ausubel et al. ed., pp. 6.3.1–6.3.6, 1987.

*Primary Examiner*—Dian C. Jacobson
*Assistant Examiner*—Hyosuk Kim
*Attorney, Agent, or Firm*—Flehr, Hohbach, Test, Albritton & Herbert; Richard F. Trecartin; Robin M. Silva

[57] ABSTRACT

Programmed cell death antagonist proteins and nucleic acids are provided, as well as expression vectors and host cells which contain the nucleic acids encoding the programmed cell death antagonist proteins.

5 Claims, 17 Drawing Sheets

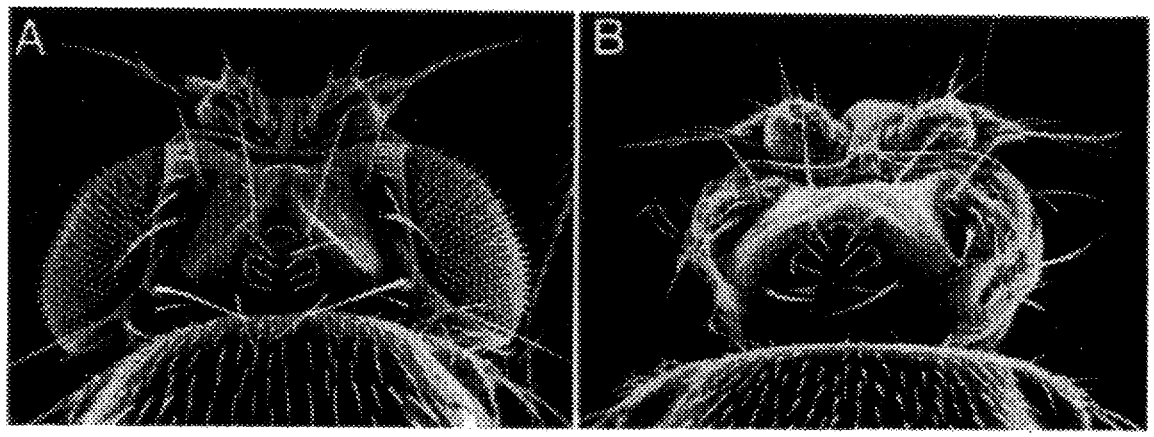
FIG._1A  FIG._1B
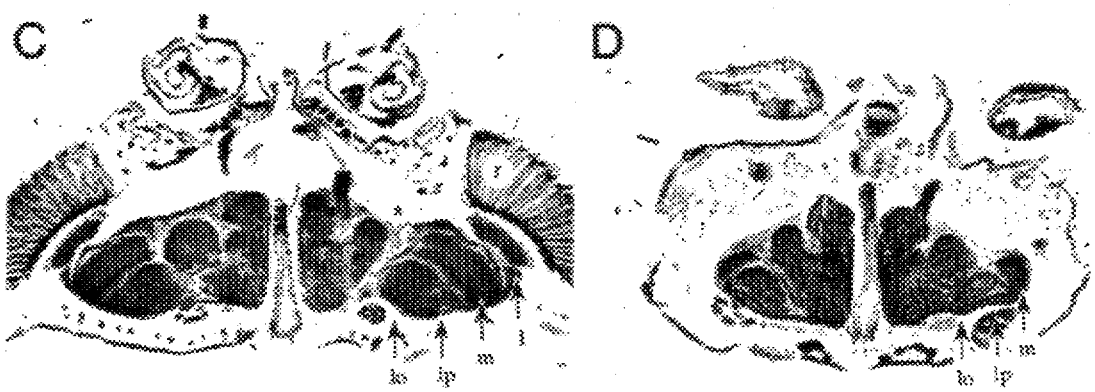
FIG._1C  FIG._1D

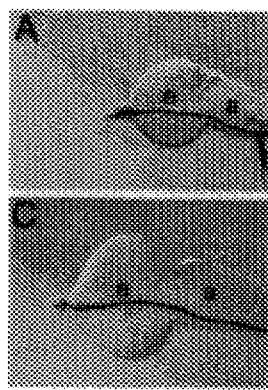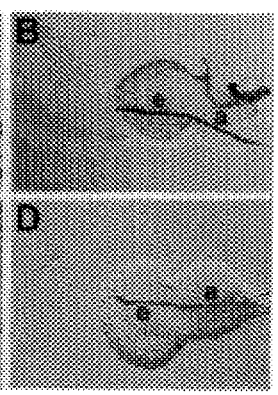
FIG._2A    FIG._2B

FIG._2C    FIG._2D
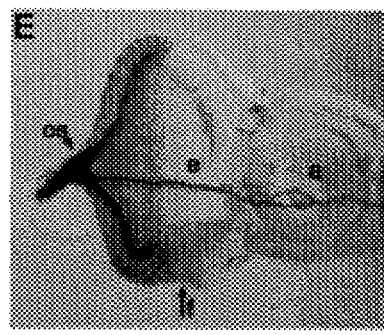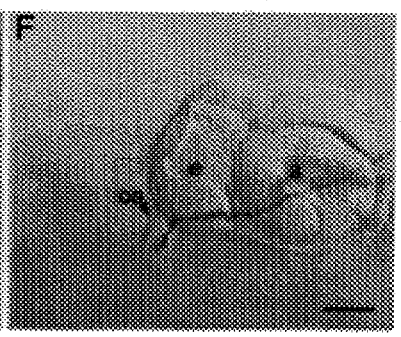
FIG._2E    FIG._2F

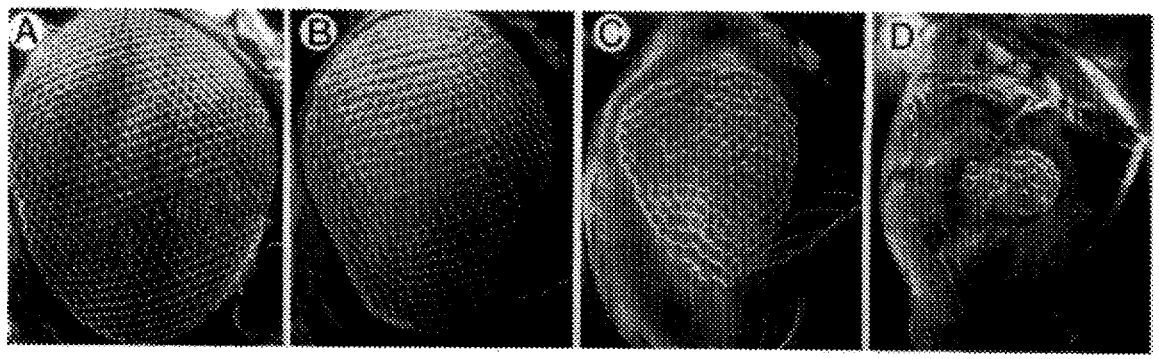
FIG._3A  FIG._3B  FIG._3C  FIG._3D
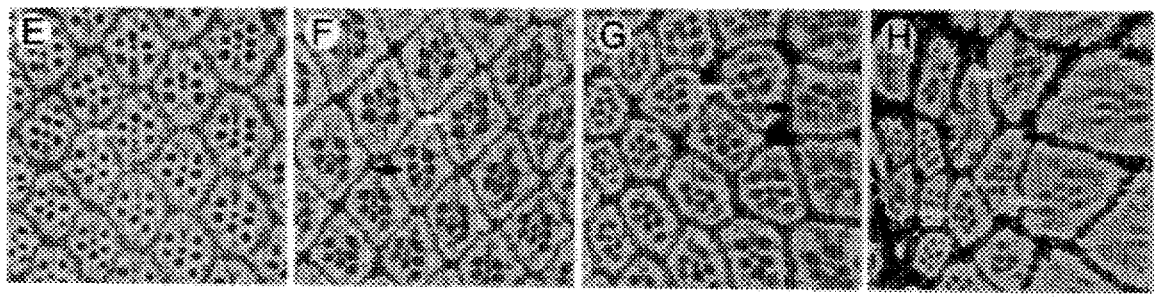
FIG._3E  FIG._3F  FIG._3G  FIG._3H

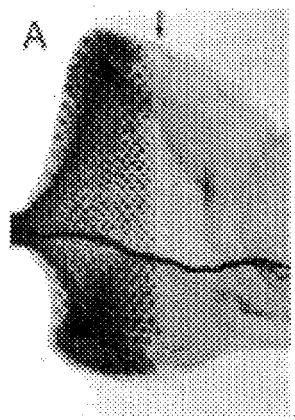 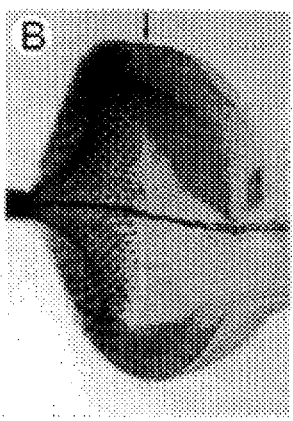  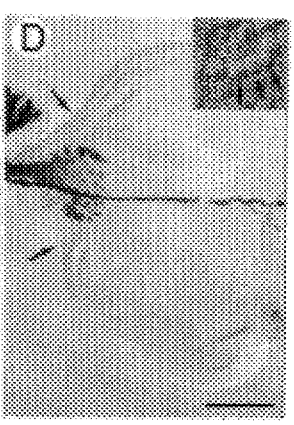
FIG._4A　　FIG._4B　　FIG._4C　　FIG._4D
  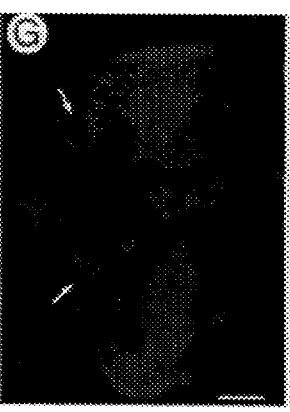 
FIG._4E　　FIG._4F　　FIG._4G　　FIG._4H

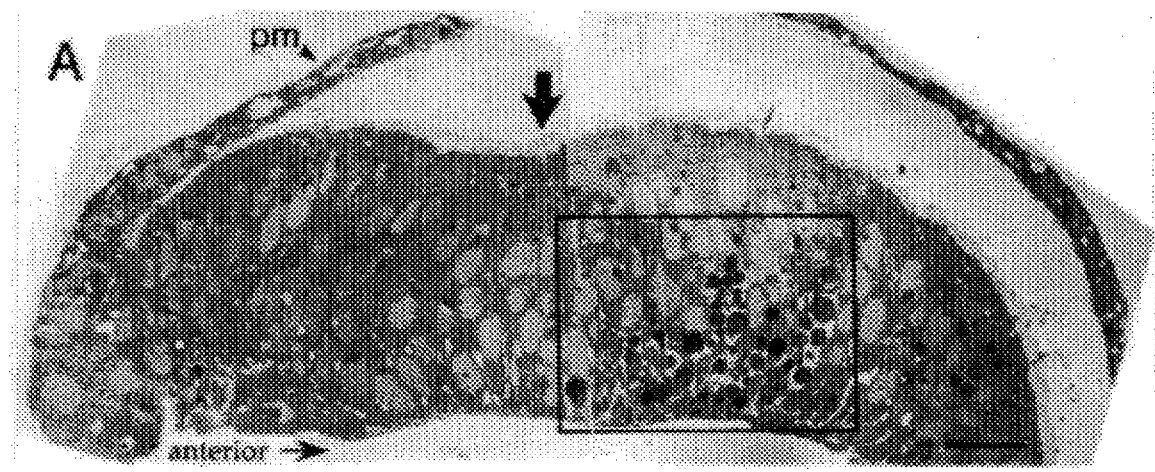
FIG._5A
FIG._5B

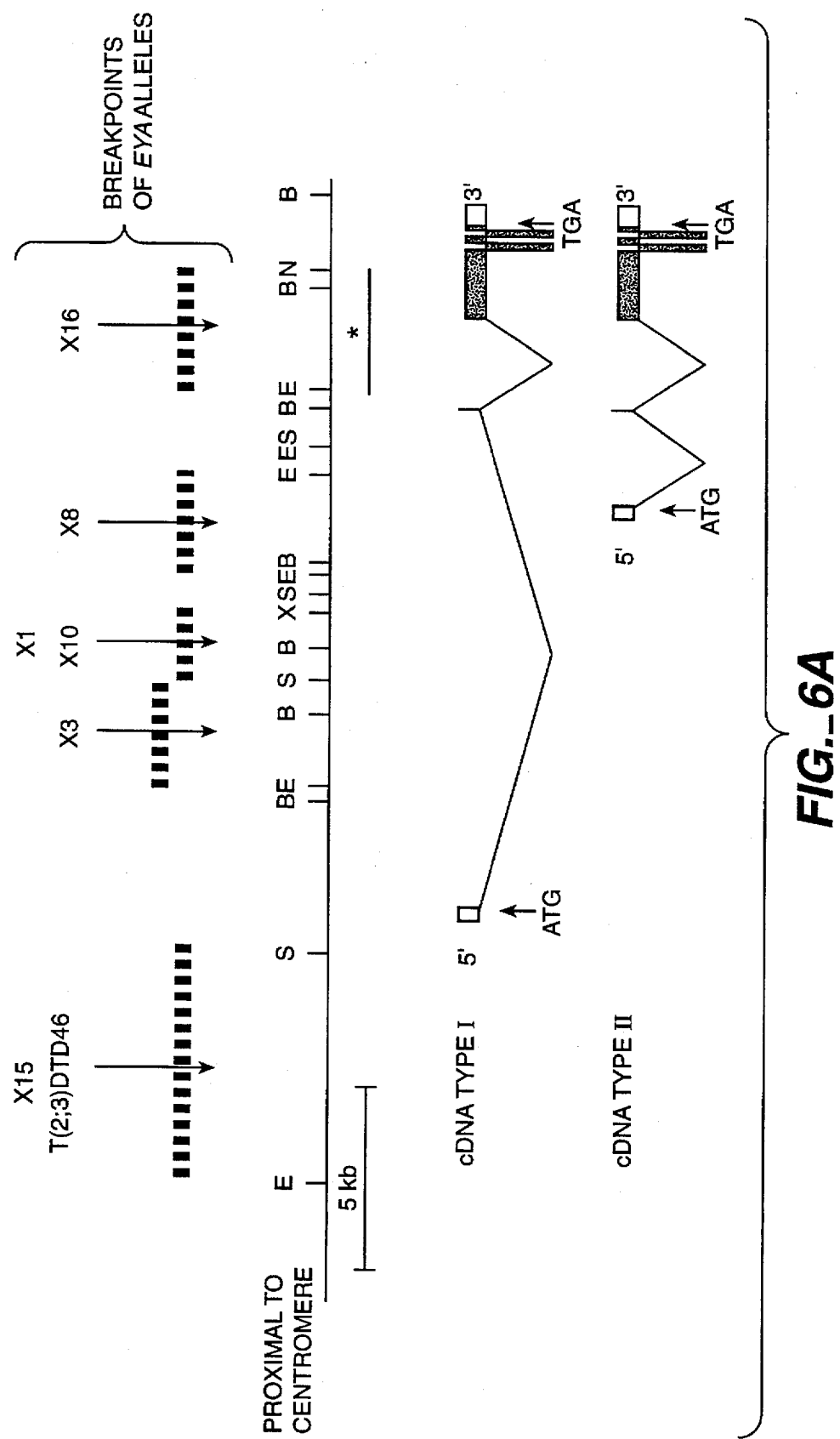
FIG._6A

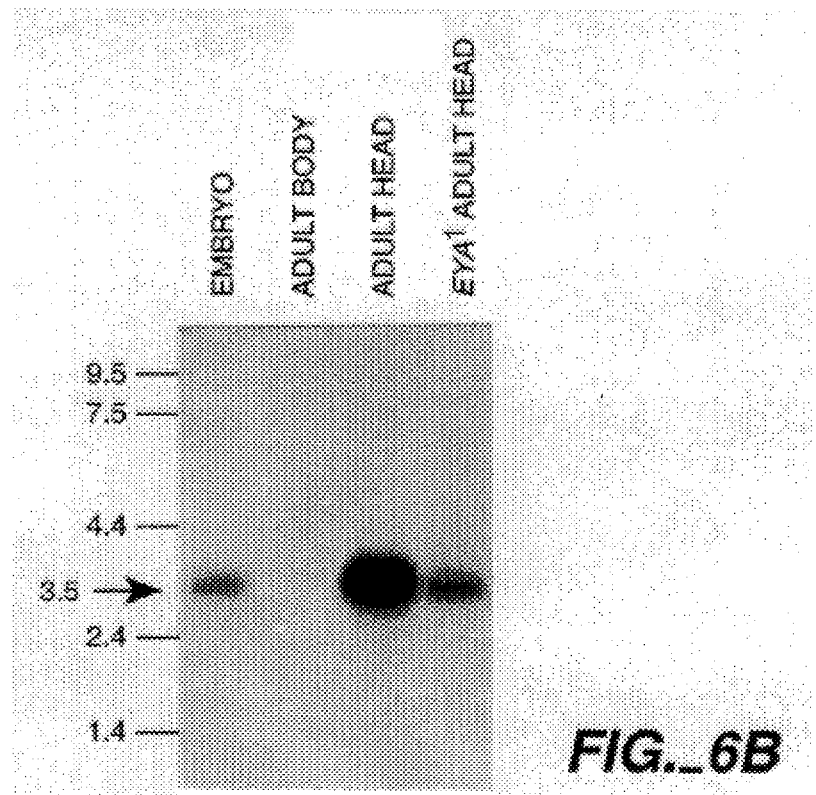
FIG._6B
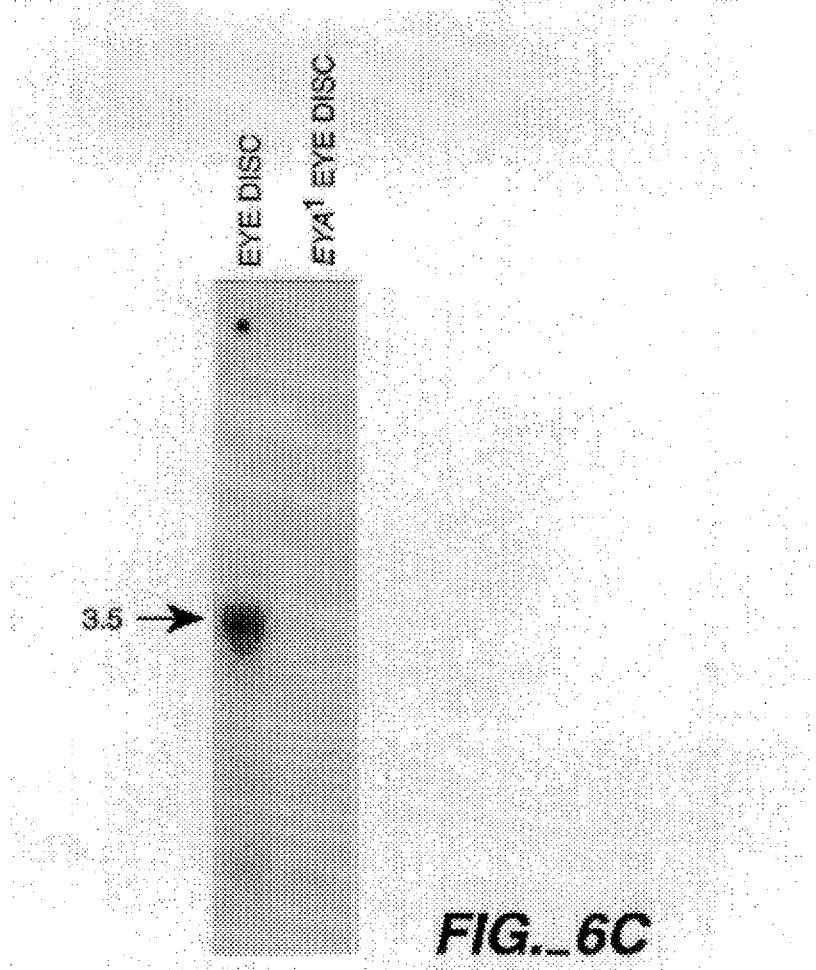
FIG._6C

Type I cDNA

5' CGTCGGCCCA GCGCTTAAAC TGAAATAAAC GCAACGAGAT ACAATTTACA TCTTTCAGAT 60
CAATTTGGCA CAAATTAATT GGCGAAACGG AACTGCTCAC TTAACGCAAT TTAATGTCCA 120
ACGTTTGTGT CGCGCGCATC GTGATAAAAA GGCTCAATTA ATTATCAATC 180
AGCAACTCAA CACTTAAAAT ATCGACTTGT GTGTGTGGTG CATTTCGAGT GTGTATAACT 240
TCTTTATATG CTTGTGAAGT CCCATCTAAAG ATGGAAGAGC ATCCCTTCCA 300
GTGGGCCATT TGACATTTCC ACTGTGCCAG GAGACGCCGT TCCAGGCATC GAGTGCCGCA 360
GGAACAGCGA CAGGAGCAGC CACAACACTT 413

TGC TAT CAA AAC TTC TCA ACG CTG GAT TAC TAC AAA GTT AAA CGT CCC 461
Cys Tyr Gln Asn Phe Ser Thr Leu Asp Tyr Tyr Lys Val Lys Arg Pro
                            15                    20
                                        >———common AAG ACA GAC ACG CAC GAT ACA CAT GAA CGC AAC CGC CTC TGC AAT CTG 509
Lys Thr Asp Thr His Asp Thr His Glu Arg Asn Arg Leu Cys Asn Leu
25                      30                      35
                                    >

TCA CAG CAG CAG CAG CAG CAG CAG CCC CAG CAG CAG ACG CAT CAG 557
Ser Gln Gln Gln Gln Gln Gln Gln Pro Gln Gln Gln Thr His Gln
40                      45                      50

CAG CAA CAG CAG CAG CAG CAG CAG CAA TCC CAT CAG CAA TCC AGC AGC 605
Gln Gln Gln Gln Gln Gln Gln Gln Ser His Gln Gln Ser His Ser Ser
55                      60                      65                      70

FIG._7A-1

```
ACC GTG TTG GCC AGC AAT GGA CCC AGT AGC GCC GGT GCC ATG GGT       653
Thr Val Leu Ala Ser Asn Gly Pro Ser Ser Ala Gly Ala Met Gly
             75                  80                  85

GTC GGT GTG GGC GGA GGC GGT GGA AGT GGT GGA GTA GGA GGC GGA       701
Val Gly Val Gly Gly Gly Gly Gly Ser Gly Gly Val Gly Gly Gly
             90                  95                 100

GTT GGC CAG TGC AGT CCG CTG GGA CTG CCG CAG AGC CAG CCG CTC       749
Val Gly Gln Cys Ser Pro Leu Gly Leu Pro Gln Ser Gln Pro Leu
            105                 110                 115

CAG CCG ACA ATA GGA TCG CTG GCC TCG CTG AGC GGT TGC AGT AAC       797
Gln Pro Thr Ile Gly Ser Leu Ala Ser Leu Ser Gly Cys Ser Asn
            120                 125                 130

GGT AAT GCC AAT CCG GTG AAC TCG AGC AGC AGC TGC AGT CTG GCC ACA   845
Gly Asn Ala Asn Pro Val Asn Ser Ser Ser Ser Cys Ser Leu Ala Thr
            135                 140                 145                 150

GCA TCC AGT TTT GCG CAG TCC GCC GGC AGT GGC AGT TTC TCC ACA TAT CAA   893
Ala Ser Ser Phe Ala Gln Ser Ala Gly Ser Gly Ser Phe Ser Thr Tyr Gln
            155                 160                 165

CAG GCT GGT GGC ACC AGC GGT GGA GTT TCT GGC GAG GAT GGC GTG GTG   941
Gln Ala Gly Gly Thr Ser Gly Gly Val Ser Gly Glu Asp Gly Val Val
            170                 175                 180

GGC GGA GCA ACT GTG ATG TCG CAC TGG ACG CAC GAT GCT ACT GGC TCG   989
Gly Gly Ala Thr Val Met Ser His Trp Thr His Asp Ala Thr Gly Ser
            185                 190                 195
```

FIG._7A-2

```
AGT GCA GCG GTC AAG TCG GAG TCC CGC AGC CCG GGC CAA GTG CAC GCA    1037
Ser Ala Ala Val Lys Ser Glu Ser Arg Ser Pro Gly Gln Val His Ala
200                 205                 210                 215

TCG CTG GAC AAC GGC TCG GTG GCC GGA TCC AAT TTG TAC GGC TGC AGC    1085
Ser Leu Asp Asn Gly Ser Val Ala Gly Ser Asn Leu Tyr Gly Cys Ser
            220                 225                 230

TCG GCC AGC AAT CCG CTG GAC GGA GGA GCA GTG GCG GTC AAC TCT TCG    1133
Ser Ala Ser Asn Pro Leu Asp Gly Gly Ala Val Ala Val Asn Ser Ser
235                 240                 245

GCA GTG GCA GCG GCA GCA ATG CAG CAG TAC GAC GGC AAA CAT GGC TAC    1181
Ala Val Ala Ala Ala Ala Met Gln Gln Tyr Asp Gly Lys His Gly Tyr
250                 255                 260

TAC TAC AAC AGC TAT GCG GCA GCT GCC ACG CCG TTC TAC TCC            1229
Tyr Tyr Asn Ser Tyr Ala Ala Ala Ala Thr Pro Pro Phe Tyr Ser
265                 270                 275

GGA TAC GGA ACT CCT TAT GCG GCG GCG ACG GCG GCA CGG CAG GCC AAG    1277
Gly Tyr Gly Thr Pro Tyr Ala Ala Ala Thr Ala Ala Arg Gln Ala Lys
280                 285                 290

ATG GAA CCC GGA GCG GCA GCT GCC GCC GCT TAC TTG ACG CCC AGC        1325
Met Glu Pro Gly Ala Ala Ala Ala Ala Ala Tyr Leu Thr Pro Ser
295                 300                 305                 310

TAT GCC GCC AGC GGC AAC AAC TCG CAG CTG TAC AGC AGT CCG TAC        1373
Tyr Ala Ala Ser Gly Asn Asn Ser Gln Leu Tyr Ser Ser Pro Tyr
            315                 320                 325
```

FIG._7A-3

```
GCC GGC TAC AAC AAC TTC GGG CAG GAC TAC GGC GGC TAC AAC    1421
Ala Gly Tyr Asn Asn Phe Gly Gln Gln Asp Tyr Gly Gly Tyr Asn
                330                    335                 340

GAG CAG TAC GGC AAC TAT TAC AGT TAC AGT TAC TCA CCG TAT GCG    1469
Glu Gln Tyr Gly Asn Tyr Tyr Ser Tyr Ser Tyr Ser Pro Tyr Ala
                345                    350                 355

GTC AGC TCG CCC AGC AGT GCG AGT CAT GGA CAT GGC TTC CAT GTG    1517
Val Ser Ser Pro Ser Ser Ala Ser His Gly His Gly Phe His Val
                360                    365                 370

GCG GCC TCC TCG AAT CTC TCC GAG AGT CCC ACG GAC ACC CAC TCG ACG    1565
Ala Ala Ser Ser Asn Leu Ser Glu Ser Pro Thr Asp Thr His Ser Thr
                375                    380                385                 390

ACG CCG GTG CAC CAG ACC ACC CAC TCC CCG CTC CCG ATC    1613
Thr Pro Val His Gln Thr Thr His Ser Pro Leu Pro Ile
                395                    400                 405

TCG CCG AGC ACT GGC TCC GGC ATT GGC CCG CTG GGC AAT GTG TCC GCG    1661
Ser Pro Ser Thr Gly Ser Gly Ile Gly Pro Leu Gly Asn Val Ser Ala
                410                    415                 420

GCA GCT GCG GCT GCC CTC AAC AGC AGC GGA GGC GGC AGT GTG GGT    1709
Ala Ala Ala Ala Ala Leu Asn Ser Ser Gly Gly Gly Ser Val Gly
                425                    430                 435

ACC GCC GGC TCT GGG GGC GTG GCA ACG AGC AAG ACC ACG CCC ACG GGT    1757
Thr Ala Gly Ser Gly Gly Val Ala (Thr) Ser Lys Thr Thr Pro (Thr) Gly
                440                    445                 450
```

*FIG._7A-4*

```
AAG ACG GGT CGG GCG CGT GGT AGA CGC CAT CAG CAG CCC AGC CCC ACC      1805
Lys Thr Gly Arg Ala Arg Gly Arg Arg His Gln Gln Pro Ser Pro Thr
      455                 460                 465                 470

AGA AGC ACT GCC TCG GAC ACC GGG AAC AGT GAG GCG GTG AAG CCA CCG      1853
Arg Ser Thr Ala Ser Asp Thr Gly Asn Ser Glu Ala Val Lys Pro Pro
              475                 480                 485

GAA CGG GTG TTC GTC TGG GAT CTG GAC GAG ACG CTC ATC ATC TTC CAC      1901
Glu Arg Val Phe Val Trp Asp Leu Asp Glu Thr Leu Ile Ile Phe His
          490                 495                 500

ACG CTG TCG GGC AGC TAT GCC AAC CGA TAC ACC AAA GAC CAC AGC          1949
Thr Leu Ser Gly Ser Tyr Ala Asn Arg Tyr Thr Lys Asp His Ser
      505                 510                 515

TCC CTG ATG ACC ATC GCC TTC CGC ATG GAG GAG ATG GTC TTC AAC ATG      1997
Ser Leu Met Thr Ile Ala Phe Arg Met Glu Glu Met Val Phe Asn Met
  520                 525                 530

GCC GAC ACG CAT TTC TTC TTC AAC GAC AAT GGC CAG GAC TGC GAC CAG GTG  2045
Ala Asp Thr His Phe Phe Phe Asn Glu Asn Gly Gln Asp Cys Asp Gln Val
535                 540                 545                 550

CAC ATC GAC GAT GTC AGC TCG GAC AGC GAC ACG TTC CAC GGC TTC GCC GCC  2093
His Ile Asp Asp Val Ser Ser Asp Ser Asp Thr Phe His Gly Phe Ala Ala
              555                 560                 565

TAC AAC TTC GCC ACG GAT GGC TTC GCC ACG AAC ACT CCA CCA GGC GCC      2141
Tyr Asn Phe Ala Thr Asp Gly Phe Ala Thr Asn Thr Pro Pro Gly Ala
          570                 575                 580
```

FIG._7A-5

```
CCG CCC AAT CTC TGC CTG CCC ACC GGT GTG AGG GGC GTC GAT TGG      2189
Pro Pro Asn Leu Cys Leu Pro Thr Gly Val Arg Gly Val Asp Trp
                585              590              595

ATG CGC AAG CTG GCC TTC CGC TAC CGC AAG ATC AAG GAC ATC TAC AAT  2237
Met Arg Lys Leu Ala Phe Arg Tyr Arg Lys Ile Lys Asp Ile Tyr Asn
            600              605              610

AGC TAT CGT GGA AAT GTT GGC ACC CTT CTG GGA CCC GGA AAA CGT GAG  2285
Ser Tyr Arg Gly Asn Val Gly Thr Leu Leu Gly Pro Gly Lys Arg Glu
615              620              625              630

GCC TGG CTA CAG ATA CGC TCG GAA ATC GAG GTG GCG ACC GAC AAC TGG  2333
Ala Trp Leu Gln Ile Arg Ser Glu Ile Glu Val Ala Thr Asp Asn Trp
            635              640              645

GCC ACG CTG GCG CTC AAG TGC CTG AGC ATG ATC TCC CAG CGG GAG AAC  2381
Ala Thr Leu Ala Leu Lys Cys Leu Ser Met Ile Ser Gln Arg Glu Asn
        650              655              660

TGC GTC AAC GTG CTG GTA ACC TCC ACG CAA CTG GCC CCG GCG CTG GCC  2429
Cys Val Asn Val Leu Val Thr Ser Thr Gln Leu Ala Pro Ala Leu Ala
        665              670              675

AAG GTC CTG CTG TTC GGA TTG GGC TTG TTC GGA ATC TTC AAC ATC GAG AAC ATT  2477
Lys Val Leu Leu Phe Gly Leu Gly Leu Phe Gly Ile Phe Asn Ile Glu Asn Ile
        680              685              690

TAC AGT GCG CAC AAA ATC GGC CAT GAA ACC TGC TAT GAG CGG ATC GTG  2525
Tyr Ser Ala His Lys Ile Gly His Glu Thr Cys Tyr Glu Arg Ile Val
695              700              705              710
```

FIG._7A-6

```
ACT CGC TTT GGG CGC AAG AGC ACC TAC Thr Val Val Ile Gly Asp Gly Asn    2573
Thr Arg Phe Gly Arg Lys Ser Thr Tyr
                        715                 720                 725

GAG GAG ACC GCC GCC AAG GCC ATG AAC TTC CCC TTC TGG CGC ATC    2621
Glu Glu Thr Ala Ala Lys Ala Met Asn Phe Pro Phe Trp Arg Ile
                730                 735                 740

TCC GCC CAC AGC GAC ATT CGC GCC CTC TAC ACT GCC CTC GAC ATG GGC    2669
Ser Ala His Ser Asp Ile Arg Ala Leu Tyr Thr Ala Leu Asp Met Gly
                745                 750                 755

TTC TTA TGA A AGGCCAAACT GTAAGGGATT CGAAGCGGTT TTGAGTACAA    2719
Phe Leu *
    760

ACAGCAAAAT GTTTAATTAA TTTATTAAAA TATGTATGTG TGTGTGTGCG TGTGAGACAA    2779

GCAACAAATG GAAACTGTAA ACCAGCGCAA AATAATTTAA TTATTTTGTT TAAACATTTA    2839

TCATTTAACG CCAAGACTTT TTGTATTATA TAGTTTTTAA ACACCTAATC AACGATCGTA    2899

ACAATTCTCG CACGAAGTTG TTCAAGTGTA TAATTAACAA GTAAATAAAT TAACGATATA    2959

CATACATACG TACGTATTTA GCACCCTAGA GTAGCAAATA ATAACAGACC GATACGCATC    3019

CTGGCTGGAG AAGCGGAGCA AACACAACAA AAATTAGTTT AAAGTTCTTA GTTTAAAAGC    3079

CGAAGCATAA TTATAATGAG TATAAATAAT TCGACAAAGC CGTAGTATTC AAATTTTAAA    3139

TAACTATTAT ATAGCTGCAT ATATTAAACT ATATTTAAAA TATAAAACCA AGTAATAAAA    3199

GAGCAAATCC AACAGCAACG CACTCTATTA AA    3231
```

FIG._7A-7

Type II cDNA

```
5' GAGCGCTACG GGAACGGTCG ATCCGCCCGA AGTCGGCAGAT AAAAAACCTA CCAGATACAT        60
   TTCGTTCGTT CTGAAACGCT ATAACTAAAT ATATATTCGA TTTCAAAACA TCGACCATAC       120
   ATTAACTACC TGAAACGGTC GAGTTCACTA ACCCGCCACG CGTGTGTGTT TTTGTGTGTG       180
   TTGCAAGTGA AAGTAATCGC AAGTCCACAG A ATG GTC ACC CTA ATG CCA TAC          232
                                     Met Val Thr Leu Met Pro Tyr
                                      1                       5

AAC TAC GCT GCC CCG CGA TGC GGA TTA ATT GAC AAA ATG ATC GAG CCA         280
   Asn Tyr Ala Ala Pro Arg Cys Gly Leu Ile Asp Lys Met Ile Glu Pro
                  10                          15                  20
             ∨ ─► common
   AAG GTT AAA CGT CCC AAG ACA GAC CAC ACG GAT ACA CAT GAA CGC AAC         328
   Lys Val Lys Arg Pro Lys Thr Asp His Thr Asp Thr His Glu Arg Asn
            25                          30                      35
   ∨
   CGC CTC TGC AAT CTG TCA CAG                                             349
   Arg Leu Cys Asn Leu Ser Gln
        40                  45
```

FIG._7B

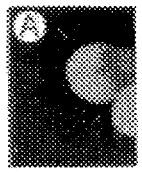
FIG._8A
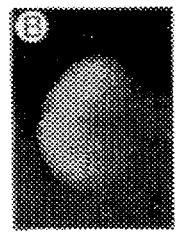
FIG._8B
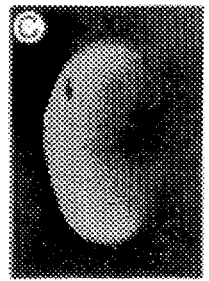
FIG._8C
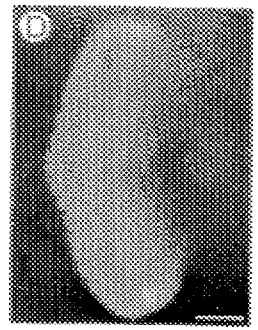
FIG._8D
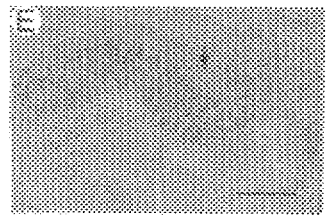
FIG._8E
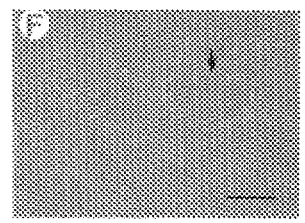
FIG._8F
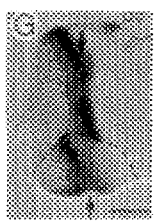
FIG._8G

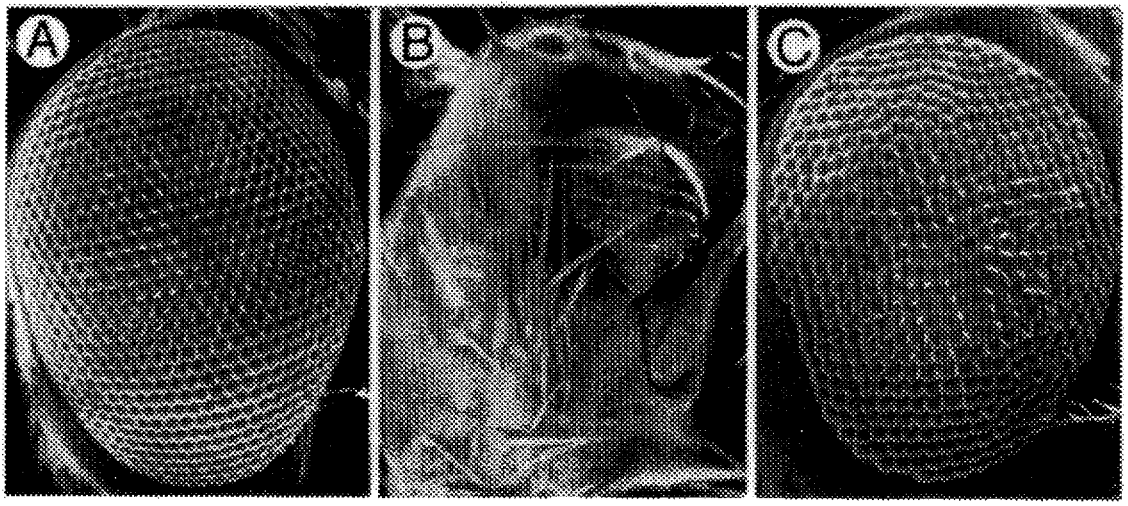
FIG._9A  FIG._9B  FIG. 9C
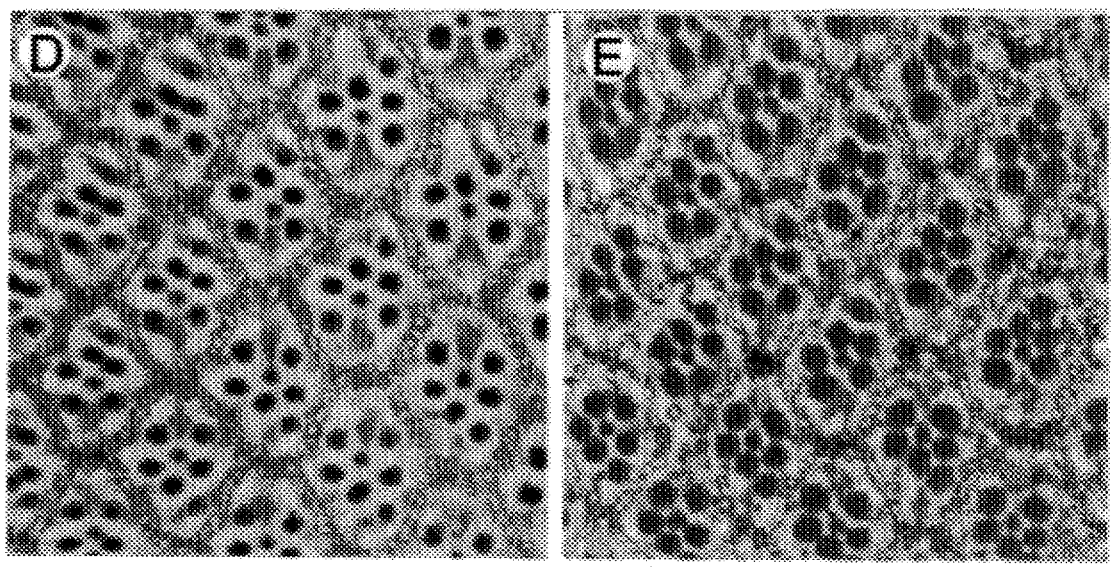
FIG._9D  FIG._9E

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
    ( A ) LENGTH: 3231 base pairs
    ( B ) TYPE: nucleic acid
    ( C ) STRANDEDNESS: double
    ( D ) TOPOLOGY: unknown ( x i ) SEQUENCE DESCRIPTION: SEQ ID NO:1:

```
CGTCGGCCCA  GCGCTTAAAC  TGAAATAAAC  GCAACGAGAT  ACAATTTACA  TCTTTCAGAT    60

CAATTTGGCA  CAAATTAATT  GGCGAAACGG  AACTGCTCAC  TTAACGCAAT  TTAATGTCCA   120

ACGTTTGTGT  CGCGCGCATC  GTGATAAAAA  TAACACAATA  GGCTCAATTA  ATTATCAATC   180

AGCAACTCAA  CACTTAAAAT  ATCGACTTGT  GTGTGTGGTG  CATTTCGAGT  GTGTATAACT   240

TCTTTATATG  CTTGTGAAGT  CCACTTAAAG  CCCATCTGCC  ATGGAAGAGC  ATCCCTTCCA   300

GTGGGCCATT  TGACATTTCC  ACTGTGCCAG  GAGACGCCGT  TCCAGGCATC  GAGTGCCGCA   360

GGAACAGCGA  CAGGAGCAGC  CACAACACTT  GGAAT ATG TTG TAT AAT GTG CCG        413
                                        Met Leu Tyr Asn Val Pro
                                         1               5

TGC TAT CAA AAC TTC TCA ACG CTG GAT TAC TAC AAA GTT AAA CGT CCC          461
Cys Tyr Gln Asn Phe Ser Thr Leu Asp Tyr Tyr Lys Val Lys Arg Pro
             10                  15                  20

AAG ACA GAC CAC ACG GAT ACA CAT GAA CGC AAC CGC CTC TGC AAT CTG          509
Lys Thr Asp His Thr Asp Thr His Glu Arg Asn Arg Leu Cys Asn Leu
         25                  30                  35

TCA CAG CAG CAG CAG CAA CAG CAA CCC CAG CAG CAA CAG ACG CAT CAG          557
Ser Gln Gln Gln Gln Gln Gln Gln Pro Gln Gln Gln Gln Thr His Gln
     40                  45                  50

CAG CAA CAA CAG CAG CAG CAG CAA TCC CAT CAG CAA TCC CAT TCC AGC          605
Gln Gln Gln Gln Gln Gln Gln Gln Ser His Gln Gln Ser His Ser Ser
 55                  60                  65                  70

ACC GTG TTG GCC AGC AAT GGA CCC AGT AGC GCC GGT GCC GGC ATG GGT          653
Thr Val Leu Ala Ser Asn Gly Pro Ser Ser Ala Gly Ala Gly Met Gly
                 75                  80                  85

GTC GGT GTG GGC GGA GGC GGT GGC AGT GGA GGA GGA GTA GGA GGC GGA          701
Val Gly Val Gly Gly Gly Gly Gly Ser Gly Gly Gly Val Gly Gly Gly
             90                  95                 100

GTT GGC CAG TGC AGT CCG CTG GGA CTG CCG CCG CAG AGC CAG CCG CTC          749
Val Gly Gln Cys Ser Pro Leu Gly Leu Pro Pro Gln Ser Gln Pro Leu
        105                 110                 115

CAG CCG ACA ATA GGA TCG CTG GCC TCG CTG AGC GGT CAC TAC TCG AAC          797
Gln Pro Thr Ile Gly Ser Leu Ala Ser Leu Ser Gly His Tyr Ser Asn
    120                 125                 130

GGT AAT GCC AAT CCG AAT GTG AAC TCG AGC AGC TGC AGT CTG GCC ACA          845
Gly Asn Ala Asn Pro Asn Val Asn Ser Ser Ser Cys Ser Leu Ala Thr
135                 140                 145                 150

GCA TCC AGT TTT GCG CAG TCC GCC GGC AGC AGT TTC TCC ACA TAT CAA          893
Ala Ser Ser Phe Ala Gln Ser Ala Gly Ser Ser Phe Ser Thr Tyr Gln
                155                 160                 165

CAG GCT GGT GGC ACC AGC GGT GGA GTT TCT GGC GAG GAT GGC GTG GTG          941
Gln Ala Gly Gly Thr Ser Gly Gly Val Ser Gly Glu Asp Gly Val Val
            170                 175                 180

GGC GGA GCA ACT GTG ATG TCG CAC TGG ACG CAC GAT GGC ACT GGC TCG          989
Gly Gly Ala Thr Val Met Ser His Trp Thr His Asp Gly Thr Gly Ser
```

-continued

|  | 185 |  |  |  |  | 190 |  |  |  |  | 195 |  |  |  |  |  |
|---|---|---|---|---|---|---|---|---|---|---|---|---|---|---|---|---|
| AGT | GCA | GCG | GTC | AAG | TCG | GAG | TCC | CGC | AGC | CCG | GGC | CAA | GTG | CAC | GCA | 1037 |
| Ser | Ala | Ala | Val | Lys | Ser | Glu | Ser | Arg | Ser | Pro | Gly | Gln | Val | His | Ala |  |
| 200 |  |  |  |  | 205 |  |  |  |  | 210 |  |  |  |  |  |  |
| TCG | CTG | GAC | AAC | GGC | TCG | GTG | GCC | GGA | TCC | AAT | TTG | TAC | GGC | TGC | AGC | 1085 |
| Ser | Leu | Asp | Asn | Gly | Ser | Val | Ala | Gly | Ser | Asn | Leu | Tyr | Gly | Cys | Ser |  |
| 215 |  |  |  |  | 220 |  |  |  |  | 225 |  |  |  |  | 230 |  |
| TCG | GCC | AGC | AAT | CCG | CTG | GAC | GGA | GGA | GCA | GTG | GCG | GTC | AAC | TCT | TCG | 1133 |
| Ser | Ala | Ser | Asn | Pro | Leu | Asp | Gly | Gly | Ala | Val | Ala | Val | Asn | Ser | Ser |  |
|  |  |  |  | 235 |  |  |  |  | 240 |  |  |  |  | 245 |  |  |
| GCA | GTG | GCA | GCG | GCA | GCA | GCA | GCG | GTC | TAC | GAC | GGC | AAA | CAT | GAC | TAC | 1181 |
| Ala | Val | Ala | Ala | Ala | Ala | Ala | Ala | Val | Tyr | Asp | Gly | Lys | His | Asp | Tyr |  |
|  |  |  | 250 |  |  |  |  | 255 |  |  |  |  | 260 |  |  |  |
| TAC | TAC | TAC | AAC | AGC | ATG | CAG | CAG | TAC | ACG | CCG | CCG | CCC | TTC | TAC | TCC | 1229 |
| Tyr | Tyr | Tyr | Asn | Ser | Met | Gln | Gln | Tyr | Thr | Pro | Pro | Pro | Phe | Tyr | Ser |  |
|  |  | 265 |  |  |  |  | 270 |  |  |  |  | 275 |  |  |  |  |
| GGA | TAC | GGA | ACT | CCT | TAT | GCG | GCG | GCA | ACG | GCG | GCA | CGG | CAG | GCC | AAG | 1277 |
| Gly | Tyr | Gly | Thr | Pro | Tyr | Ala | Ala | Ala | Thr | Ala | Ala | Arg | Gln | Ala | Lys |  |
|  | 280 |  |  |  |  | 285 |  |  |  |  | 290 |  |  |  |  |  |
| ATG | GAA | CCC | GGA | GCG | GCA | GCT | GCG | GCG | GCT | GCC | TAC | TTG | ACG | CCC | AGC | 1325 |
| Met | Glu | Pro | Gly | Ala | Ala | Ala | Ala | Ala | Ala | Ala | Tyr | Leu | Thr | Pro | Ser |  |
| 295 |  |  |  |  | 300 |  |  |  |  | 305 |  |  |  |  | 310 |  |
| TAT | GCC | GCC | AGC | GGC | AAC | AAC | AAC | TCG | CAG | CTG | TAC | AGC | AGT | CCG | TAC | 1373 |
| Tyr | Ala | Ala | Ser | Gly | Asn | Asn | Asn | Ser | Gln | Leu | Tyr | Ser | Ser | Pro | Tyr |  |
|  |  |  |  | 315 |  |  |  |  | 320 |  |  |  |  | 325 |  |  |
| GCC | GGC | TAC | AAC | AAC | TTC | GGG | CAG | CAG | GAC | TAC | GGC | GGC | TAC | TAC | AAC | 1421 |
| Ala | Gly | Tyr | Asn | Asn | Phe | Gly | Gln | Gln | Asp | Tyr | Gly | Gly | Tyr | Tyr | Asn |  |
|  |  |  | 330 |  |  |  |  | 335 |  |  |  |  | 340 |  |  |  |
| GAG | CAG | TAC | GGC | AAC | TAT | TAC | AGT | CCG | GCC | AAC | TAC | TCA | CCG | TAT | GCG | 1469 |
| Glu | Gln | Tyr | Gly | Asn | Tyr | Tyr | Ser | Pro | Ala | Asn | Tyr | Ser | Pro | Tyr | Ala |  |
|  |  | 345 |  |  |  |  | 350 |  |  |  |  | 355 |  |  |  |  |
| GTC | AGC | TCG | CCC | AGC | TCG | AGT | GCG | AGT | CAT | GGA | CAT | GGC | TTC | CAT | GTG | 1517 |
| Val | Ser | Ser | Pro | Ser | Ser | Ser | Ala | Ser | His | Gly | His | Gly | Phe | His | Val |  |
|  | 360 |  |  |  |  | 365 |  |  |  |  | 370 |  |  |  |  |  |
| GCG | GCC | TCC | TCG | AAT | CTC | TCC | GAG | AGT | CCC | ACG | GAC | ACC | CAC | TCG | ACG | 1565 |
| Ala | Ala | Ser | Ser | Asn | Leu | Ser | Glu | Ser | Pro | Thr | Asp | Thr | His | Ser | Thr |  |
| 375 |  |  |  |  | 380 |  |  |  |  | 385 |  |  |  |  | 390 |  |
| ACG | CCG | GTG | CAC | CAG | ACC | ACC | CAC | TCG | CCG | CAC | TCC | CCG | CTC | CCG | ATC | 1613 |
| Thr | Pro | Val | His | Gln | Thr | Thr | His | Ser | Pro | His | Ser | Pro | Leu | Pro | Ile |  |
|  |  |  |  | 395 |  |  |  |  | 400 |  |  |  |  | 405 |  |  |
| TCG | CCG | AGC | ACT | GGC | TCC | GGC | ATT | GGC | CCG | CTG | GGC | AAT | GTG | TCC | GCG | 1661 |
| Ser | Pro | Ser | Thr | Gly | Ser | Gly | Ile | Gly | Pro | Leu | Gly | Asn | Val | Ser | Ala |  |
|  |  |  | 410 |  |  |  |  | 415 |  |  |  |  | 420 |  |  |  |
| GCA | GCT | GCG | GCC | GCT | GCT | CTC | AAC | TCG | AGC | GGA | GGC | AGC | AGT | GTG | GGT | 1709 |
| Ala | Ala | Ala | Ala | Ala | Ala | Leu | Asn | Ser | Ser | Gly | Gly | Ser | Ser | Val | Gly |  |
|  |  | 425 |  |  |  |  | 430 |  |  |  |  | 435 |  |  |  |  |
| ACC | GCC | GGC | TCT | GGG | GGC | GTG | GCA | ACG | AGC | AAG | ACC | ACG | CCC | ACG | GGT | 1757 |
| Thr | Ala | Gly | Ser | Gly | Gly | Val | Ala | Thr | Ser | Lys | Thr | Thr | Pro | Thr | Gly |  |
|  | 440 |  |  |  |  | 445 |  |  |  |  | 450 |  |  |  |  |  |
| AAG | ACG | GGT | CGG | GCG | CGT | GGT | AGA | CGC | CAT | CAG | CAG | CCC | AGC | CCC | ACC | 1805 |
| Lys | Thr | Gly | Arg | Ala | Arg | Gly | Arg | Arg | His | Gln | Gln | Pro | Ser | Pro | Thr |  |
| 455 |  |  |  |  | 460 |  |  |  |  | 465 |  |  |  |  | 470 |  |
| AGA | AGC | ACT | GCC | TCG | GAC | ACC | GGG | AAC | AGT | GAG | GCG | GTG | AAG | CCA | CCG | 1853 |
| Arg | Ser | Thr | Ala | Ser | Asp | Thr | Gly | Asn | Ser | Glu | Ala | Val | Lys | Pro | Pro |  |
|  |  |  |  | 475 |  |  |  |  | 480 |  |  |  |  | 485 |  |  |
| GAA | CGG | GTG | TTC | GTC | TGG | GAT | CTG | GAC | GAG | ACG | CTC | ATC | ATC | TTC | CAC | 1901 |
| Glu | Arg | Val | Phe | Val | Trp | Asp | Leu | Asp | Glu | Thr | Leu | Ile | Ile | Phe | His |  |
|  |  |  | 490 |  |  |  |  | 495 |  |  |  |  | 500 |  |  |  |
| ACG | CTG | CTG | TCG | GGC | AGC | TAT | GCC | AAC | CGA | TAC | ACC | AAA | GAC | CAC | AGC | 1949 |
| Thr | Leu | Leu | Ser | Gly | Ser | Tyr | Ala | Asn | Arg | Tyr | Thr | Lys | Asp | His | Ser |  |

|  |  |  |  |  |  |  |  |  |  |  |  |  |  |  |  |  |
|---|---|---|---|---|---|---|---|---|---|---|---|---|---|---|---|---|
| | | 505 | | | | 510 | | | | | | 515 | | | | |
| TCC | CTG | ATG | ACC | ATC | GCC | TTC | CGC | ATG | GAG | GAG | ATG | GTC | TTC | AAC | ATG | 1997 |
| Ser | Leu | Met | Thr | Ile | Ala | Phe | Arg | Met | Glu | Glu | Met | Val | Phe | Asn | Met | |
| 520 | | | | | 525 | | | | | 530 | | | | | | |
| GCC | GAC | ACG | CAT | TTC | TTC | TTC | AAC | GAG | ATC | GAG | GAG | TGC | GAC | CAG | GTG | 2045 |
| Ala | Asp | Thr | His | Phe | Phe | Phe | Asn | Glu | Ile | Glu | Glu | Cys | Asp | Gln | Val | |
| 535 | | | | | 540 | | | | | 545 | | | | | 550 | |
| CAC | ATC | GAC | GAT | GTC | AGC | TCG | GAC | GAC | AAT | GGC | CAG | GAC | CTG | AGC | GCC | 2093 |
| His | Ile | Asp | Asp | Val | Ser | Ser | Asp | Asp | Asn | Gly | Gln | Asp | Leu | Ser | Ala | |
| | | | | 555 | | | | | 560 | | | | | 565 | | |
| TAC | AAC | TTC | GCC | ACG | GAT | GGC | TTC | CAC | ACG | AAC | ACT | CCA | CCA | GGC | GCC | 2141 |
| Tyr | Asn | Phe | Ala | Thr | Asp | Gly | Phe | His | Thr | Asn | Thr | Pro | Pro | Gly | Ala | |
| | | 570 | | | | | 575 | | | | | 580 | | | | |
| CCG | CCC | AAT | CTC | TGC | CTG | CCC | ACC | GGT | GTG | AGG | GGC | GGC | GTC | GAT | TGG | 2189 |
| Pro | Pro | Asn | Leu | Cys | Leu | Pro | Thr | Gly | Val | Arg | Gly | Gly | Val | Asp | Trp | |
| | | 585 | | | | | 590 | | | | | 595 | | | | |
| ATG | CGC | AAG | CTG | GCC | TTC | CGC | TAC | CGC | AAG | ATC | AAG | GAC | ATC | TAC | AAT | 2237 |
| Met | Arg | Lys | Leu | Ala | Phe | Arg | Tyr | Arg | Lys | Ile | Lys | Asp | Ile | Tyr | Asn | |
| 600 | | | | | 605 | | | | | 610 | | | | | | |
| AGC | TAT | CGT | GGA | AAT | GTT | GGC | ACC | CTT | CTG | GGA | CCC | GGA | AAA | CGT | GAG | 2285 |
| Ser | Tyr | Arg | Gly | Asn | Val | Gly | Thr | Leu | Leu | Gly | Pro | Gly | Lys | Arg | Glu | |
| 615 | | | | | 620 | | | | | 625 | | | | | 630 | |
| GCC | TGG | CTA | CAG | ATA | CGC | TCG | GAA | ATC | GAG | GTG | GCG | ACC | GAC | AAC | TGG | 2333 |
| Ala | Trp | Leu | Gln | Ile | Arg | Ser | Glu | Ile | Glu | Val | Ala | Thr | Asp | Asn | Trp | |
| | | | | 635 | | | | | 640 | | | | | 645 | | |
| GCC | ACG | CTG | GCG | CTC | AAG | TGC | CTG | AGC | ATG | ATC | TCC | CAG | CGG | GAG | AAC | 2381 |
| Ala | Thr | Leu | Ala | Leu | Lys | Cys | Leu | Ser | Met | Ile | Ser | Gln | Arg | Glu | Asn | |
| | | | 650 | | | | | 655 | | | | | 660 | | | |
| TGC | GTC | AAC | GTG | CTG | GTA | ACC | TCC | ACG | CAA | CTG | GCC | CCG | GCG | CTG | GCC | 2429 |
| Cys | Val | Asn | Val | Leu | Val | Thr | Ser | Thr | Gln | Leu | Ala | Pro | Ala | Leu | Ala | |
| | | 665 | | | | | 670 | | | | | 675 | | | | |
| AAG | GTC | CTG | CTG | TTC | GGA | TTG | GGC | GGC | ATC | TTC | AAC | ATC | GAG | AAC | ATT | 2477 |
| Lys | Val | Leu | Leu | Phe | Gly | Leu | Gly | Gly | Ile | Phe | Asn | Ile | Glu | Asn | Ile | |
| | 680 | | | | | 685 | | | | | 690 | | | | | |
| TAC | AGT | GCG | CAC | AAA | ATC | GGC | CAT | GAA | ACC | TGC | TAT | GAG | CGG | ATC | GTG | 2525 |
| Tyr | Ser | Ala | His | Lys | Ile | Gly | His | Glu | Thr | Cys | Tyr | Glu | Arg | Ile | Val | |
| 695 | | | | | 700 | | | | | 705 | | | | | 710 | |
| ACT | CGC | TTT | GGG | CGC | AAG | AGC | ACC | TAC | GTG | GTG | ATT | GGG | GAT | GGG | AAC | 2573 |
| Thr | Arg | Phe | Gly | Arg | Lys | Ser | Thr | Tyr | Val | Val | Ile | Gly | Asp | Gly | Asn | |
| | | | | 715 | | | | | 720 | | | | | 725 | | |
| GAG | GAG | GAG | ACC | GCC | GCC | AAG | GCC | ATG | AAC | TTC | CCC | TTC | TGG | CGC | ATC | 2621 |
| Glu | Glu | Glu | Thr | Ala | Ala | Lys | Ala | Met | Asn | Phe | Pro | Phe | Trp | Arg | Ile | |
| | | | 730 | | | | | 735 | | | | | 740 | | | |
| TCC | GCC | CAC | AGC | GAC | ATT | CGC | GCC | CTC | TAC | ACT | GCC | CTC | GAC | ATG | GGC | 2669 |
| Ser | Ala | His | Ser | Asp | Ile | Arg | Ala | Leu | Tyr | Thr | Ala | Leu | Asp | Met | Gly | |
| | 745 | | | | | 750 | | | | | 755 | | | | | |
| TTC | TTA | TGA | A AGGCCAAACT | | GTAAGGGATT | | | CGAAGCGGTT | | | TTGAGTACAA | | | | | 2719 |
| Phe | Leu | * | | | | | | | | | | | | | | |
| | | 760 | | | | | | | | | | | | | | |

ACAGCAAAAT GTTTAATTAA TTTATTAAAA TATGTATGTG TGTGTGTGCG TGTGAGACAA 2779

GCAACAAATG GAAACTGTAA ACCAGCGCAA AATAATTTAA TTATTTTGTT TAAACATTTA 2839

TCATTTAACG CCAAGACTTT TTGTATTATA TAGTTTTTAA ACACCTAATC AACGATCGTA 2899

ACAATTCTCG CACGAAGTTG TTCAAGTGTA TAATTAACAA GTAAATAAAT TAACGATATA 2959

CATACATACG TACGTATTTA GCACCCTAGA GTAGCAAATA ATAACAGACC GATACGCATC 3019

CTGGCTGGAG AAGCGGAGCA AACACAACAA AAATTAGTTT AAAGTTCTTA GTTTAAAAGC 3079

CGAAGCATAA TTATAATGAG TATAAATAAT TCGACAAAGC CGTAGTATTC AAATTTTAAA 3139

```
TAACTATTAT ATAGCTGCAT ATATTAAACT ATATTTAAAA TATAAAACCA AGTAATAAAA    3199

GAGCAAATCC AACAGCAACG CACTCTATTA AA                                  3231
```

( 2 ) INFORMATION FOR SEQ ID NO:2:

( i ) SEQUENCE CHARACTERISTICS:
        ( A ) LENGTH: 760 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Leu Tyr Asn Val Pro Cys Tyr Gln Asn Phe Ser Thr Leu Asp Tyr
 1               5                  10                  15

Tyr Lys Val Lys Arg Pro Lys Thr Asp His Thr Asp Thr His Glu Arg
                20                  25                  30

Asn Arg Leu Cys Asn Leu Ser Gln Gln Gln Gln Gln Gln Gln Pro Gln
            35                  40                  45

Gln Gln Gln Thr His Gln Gln Gln Gln Gln Gln Gln Gln Ser His
        50                  55                  60

Gln Gln Ser His Ser Ser Thr Val Leu Ala Ser Asn Gly Pro Ser Ser
 65                  70                  75                  80

Ala Gly Ala Gly Met Gly Val Gly Val Gly Gly Gly Gly Ser Gly
                85                  90                  95

Gly Gly Val Gly Gly Gly Val Gly Gln Cys Ser Pro Leu Gly Leu Pro
            100                 105                 110

Pro Gln Ser Gln Pro Leu Gln Pro Thr Ile Gly Ser Leu Ala Ser Leu
        115                 120                 125

Ser Gly His Tyr Ser Asn Gly Asn Ala Asn Pro Asn Val Asn Ser Ser
    130                 135                 140

Ser Cys Ser Leu Ala Thr Ala Ser Ser Phe Ala Gln Ser Ala Gly Ser
145                 150                 155                 160

Ser Phe Ser Thr Tyr Gln Gln Ala Gly Gly Thr Ser Gly Gly Val Ser
                165                 170                 175

Gly Glu Asp Gly Val Val Gly Gly Ala Thr Val Met Ser His Trp Thr
            180                 185                 190

His Asp Gly Thr Gly Ser Ser Ala Ala Val Lys Ser Glu Ser Arg Ser
        195                 200                 205

Pro Gly Gln Val His Ala Ser Leu Asp Asn Gly Ser Val Ala Gly Ser
    210                 215                 220

Asn Leu Tyr Gly Cys Ser Ser Ala Ser Asn Pro Leu Asp Gly Gly Ala
225                 230                 235                 240

Val Ala Val Asn Ser Ser Ala Val Ala Ala Ala Ala Ala Val Tyr
                245                 250                 255

Asp Gly Lys His Asp Tyr Tyr Tyr Asn Ser Met Gln Gln Tyr Thr
            260                 265                 270

Pro Pro Pro Phe Tyr Ser Gly Tyr Gly Thr Pro Tyr Ala Ala Ala Thr
        275                 280                 285

Ala Ala Arg Gln Ala Lys Met Glu Pro Gly Ala Ala Ala Ala Ala
    290                 295                 300

Ala Tyr Leu Thr Pro Ser Tyr Ala Ala Ser Gly Asn Asn Asn Ser Gln
305                 310                 315                 320

Leu Tyr Ser Ser Pro Tyr Ala Gly Tyr Asn Asn Phe Gly Gln Gln Asp
                325                 330                 335

Tyr Gly Gly Tyr Tyr Asn Glu Gln Tyr Gly Asn Tyr Tyr Ser Pro Ala
```

|     | 340 |     |     |     |     | 345 |     |     |     |     | 350 |     |     |
| --- | --- | --- | --- | --- | --- | --- | --- | --- | --- | --- | --- | --- | --- |
| Asn | Tyr | Ser | Pro | Tyr | Ala | Val | Ser | Ser | Pro | Ser | Ser | Ser | Ala | Ser | His |
|     |     | 355 |     |     |     |     | 360 |     |     |     |     | 365 |     |     |     |
| Gly | His | Gly | Phe | His | Val | Ala | Ser | Ser | Asn | Leu | Ser | Glu | Ser | Pro |
|     | 370 |     |     |     |     | 375 |     |     |     |     | 380 |     |     |     |
| Thr | Asp | Thr | His | Ser | Thr | Thr | Pro | Val | His | Gln | Thr | Thr | His | Ser | Pro |
| 385 |     |     |     |     |     | 390 |     |     |     |     | 395 |     |     |     | 400 |
| His | Ser | Pro | Leu | Pro | Ile | Ser | Pro | Ser | Thr | Gly | Ser | Gly | Ile | Gly | Pro |
|     |     |     |     | 405 |     |     |     |     | 410 |     |     |     |     | 415 |     |
| Leu | Gly | Asn | Val | Ser | Ala | Ala | Ala | Ala | Ala | Ala | Leu | Asn | Ser | Ser |
|     |     |     | 420 |     |     |     |     | 425 |     |     |     |     | 430 |     |     |
| Gly | Gly | Ser | Ser | Val | Gly | Thr | Ala | Gly | Ser | Gly | Gly | Val | Ala | Thr | Ser |
|     |     | 435 |     |     |     |     | 440 |     |     |     |     | 445 |     |     |     |
| Lys | Thr | Thr | Pro | Thr | Gly | Lys | Thr | Gly | Arg | Ala | Arg | Gly | Arg | Arg | His |
|     | 450 |     |     |     |     | 455 |     |     |     |     | 460 |     |     |     |     |
| Gln | Gln | Pro | Ser | Pro | Thr | Arg | Ser | Thr | Ala | Ser | Asp | Thr | Gly | Asn | Ser |
| 465 |     |     |     |     | 470 |     |     |     |     | 475 |     |     |     |     | 480 |
| Glu | Ala | Val | Lys | Pro | Pro | Glu | Arg | Val | Phe | Val | Trp | Asp | Leu | Asp | Glu |
|     |     |     |     | 485 |     |     |     |     | 490 |     |     |     |     | 495 |     |
| Thr | Leu | Ile | Ile | Phe | His | Thr | Leu | Leu | Ser | Gly | Ser | Tyr | Ala | Asn | Arg |
|     |     |     | 500 |     |     |     |     | 505 |     |     |     |     | 510 |     |     |
| Tyr | Thr | Lys | Asp | His | Ser | Ser | Leu | Met | Thr | Ile | Ala | Phe | Arg | Met | Glu |
|     |     | 515 |     |     |     |     | 520 |     |     |     |     | 525 |     |     |     |
| Glu | Met | Val | Phe | Asn | Met | Ala | Asp | Thr | His | Phe | Phe | Phe | Asn | Glu | Ile |
|     | 530 |     |     |     |     | 535 |     |     |     |     | 540 |     |     |     |     |
| Glu | Glu | Cys | Asp | Gln | Val | His | Ile | Asp | Asp | Val | Ser | Ser | Asp | Asp | Asn |
| 545 |     |     |     |     | 550 |     |     |     |     | 555 |     |     |     |     | 560 |
| Gly | Gln | Asp | Leu | Ser | Ala | Tyr | Asn | Phe | Ala | Thr | Asp | Gly | Phe | His | Thr |
|     |     |     |     | 565 |     |     |     |     | 570 |     |     |     |     | 575 |     |
| Asn | Thr | Pro | Pro | Gly | Ala | Pro | Pro | Asn | Leu | Cys | Leu | Pro | Thr | Gly | Val |
|     |     |     | 580 |     |     |     |     | 585 |     |     |     |     | 590 |     |     |
| Arg | Gly | Gly | Val | Asp | Trp | Met | Arg | Lys | Leu | Ala | Phe | Arg | Tyr | Arg | Lys |
|     |     | 595 |     |     |     |     | 600 |     |     |     |     | 605 |     |     |     |
| Ile | Lys | Asp | Ile | Tyr | Asn | Ser | Tyr | Arg | Gly | Asn | Val | Gly | Thr | Leu | Leu |
|     | 610 |     |     |     |     | 615 |     |     |     |     | 620 |     |     |     |     |
| Gly | Pro | Gly | Lys | Arg | Glu | Ala | Trp | Leu | Gln | Ile | Arg | Ser | Glu | Ile | Glu |
| 625 |     |     |     |     | 630 |     |     |     |     | 635 |     |     |     |     | 640 |
| Val | Ala | Thr | Asp | Asn | Trp | Ala | Thr | Leu | Ala | Leu | Lys | Cys | Leu | Ser | Met |
|     |     |     |     | 645 |     |     |     |     | 650 |     |     |     |     | 655 |     |
| Ile | Ser | Gln | Arg | Glu | Asn | Cys | Val | Asn | Val | Leu | Val | Thr | Ser | Thr | Gln |
|     |     |     | 660 |     |     |     |     | 665 |     |     |     |     | 670 |     |     |
| Leu | Ala | Pro | Ala | Leu | Ala | Lys | Val | Leu | Leu | Phe | Gly | Leu | Gly | Gly | Ile |
|     |     | 675 |     |     |     |     | 680 |     |     |     |     | 685 |     |     |     |
| Phe | Asn | Ile | Glu | Asn | Ile | Tyr | Ser | Ala | His | Lys | Ile | Gly | His | Glu | Thr |
|     | 690 |     |     |     |     | 695 |     |     |     |     | 700 |     |     |     |     |
| Cys | Tyr | Glu | Arg | Ile | Val | Thr | Arg | Phe | Gly | Arg | Lys | Ser | Thr | Tyr | Val |
| 705 |     |     |     |     | 710 |     |     |     |     | 715 |     |     |     |     | 720 |
| Val | Ile | Gly | Asp | Gly | Asn | Glu | Glu | Glu | Thr | Ala | Ala | Lys | Ala | Met | Asn |
|     |     |     |     | 725 |     |     |     |     | 730 |     |     |     |     | 735 |     |
| Phe | Pro | Phe | Trp | Arg | Ile | Ser | Ala | His | Ser | Asp | Ile | Arg | Ala | Leu | Tyr |
|     |     |     | 740 |     |     |     |     | 745 |     |     |     |     | 750 |     |     |
| Thr | Ala | Leu | Asp | Met | Gly | Phe | Leu |
|     |     | 755 |     |     |     |     | 760 |

( 2 ) INFORMATION FOR SEQ ID NO:3:

( i ) SEQUENCE CHARACTERISTICS:
        ( A ) LENGTH: 349 base pairs
        ( B ) TYPE: nucleic acid
        ( C ) STRANDEDNESS: double
        ( D ) TOPOLOGY: unknown ( x i ) SEQUENCE DESCRIPTION: SEQ ID NO:3:

```
GAGCGCTACG GGAACGGTCG ATCCGCCCGA AGTCGCAGAT AAAAAACCTA CCAGATACAT        60

TTCGTTCGTT CTGAAACGCT ATAACTAAAT ATATATTCGA TTTCAAAACA TCGACCATAC       120

ATTAACTACC TGAAACGGTC GAGTTCACTA ACCCGCCACG CGTGTGTGTT TTTGTGTGTG       180

TTGCAAGTGA AAGTAATCGC AAGTCCACAG A ATG GTC ACC CTA ATG CCA TAC          232
                                   Met Val Thr Leu Met Pro Tyr
                                    1               5

AAC TAC GCT GCC CCG CGA TGC GGA TTA ATT GAC AAA ATG ATC GAG CCA         280
Asn Tyr Ala Ala Pro Arg Cys Gly Leu Ile Asp Lys Met Ile Glu Pro
            10              15              20

AAG GTT AAA CGT CCC AAG ACA GAC CAC ACG GAT ACA CAT GAA CGC AAC         328
Lys Val Lys Arg Pro Lys Thr Asp His Thr Asp Thr His Glu Arg Asn
    25              30              35

CGC CTC TGC AAT CTG TCA CAG                                             349
Arg Leu Cys Asn Leu Ser Gln
40              45
```

( 2 ) INFORMATION FOR SEQ ID NO:4:

( i ) SEQUENCE CHARACTERISTICS:
        ( A ) LENGTH: 46 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Val Thr Leu Met Pro Tyr Asn Tyr Ala Ala Pro Arg Cys Gly Leu
 1               5                  10                  15

Ile Asp Lys Met Ile Glu Pro Lys Val Lys Arg Pro Lys Thr Asp His
            20                  25                  30

Thr Asp Thr His Glu Arg Asn Arg Leu Cys Asn Leu Ser Gln
        35                  40                  45
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: unknown ( x i ) SEQUENCE DESCRIPTION: SEQ ID NO:5:

```
GCGATGCTGT CGGAATGGAC                                                    20
```

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: unknown ( x i ) SEQUENCE DESCRIPTION: SEQ ID NO:6:

```
GTTGGTTTAA GGCGCAAGAC T                                                  21
```

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: double
(D) TOPOLOGY: unknown (xi) SEQUENCE DESCRIPTION: SEQ ID NO:7:

CGAGTCGAAC GCCCGATCTC                                    20

(2) INFORMATION FOR SEQ ID NO:8:

(i) SEQUENCE CHARACTERISTICS:
(A) LENGTH: 20 base pairs
(B) TYPE: nucleic acid
(C) STRANDEDNESS: double
(D) TOPOLOGY: unknown (xi) SEQUENCE DESCRIPTION: SEQ ID NO:8:

AGGAGTCGCA TAAGGGAGAG                                    20

PROGRAMMED CELL DEATH ANTAGONIST PROTEIN

This invention was made with government support under grant numbers EY09278, awarded by the National Institute of Health, and 8908154, awarded by the National Science Foundation. The government has certain rights in the invention.

FIELD OF THE INVENTION

The invention relates to proteins involved in the prevention of programmed cell death, namely programmed cell death antagonist (PCDA) proteins.

BACKGROUND OF THE INVENTION

Cells become specified during development through sequential restriction of their potential fates. This process includes mechanisms that monitor differentiation to eliminate, by programmed cell death, cells that have inappropriate specificity or developmental capacity, or that are extraneous (Glucksmann, *Biol Rev.* 26:59–86 (1951); Saunders, *Science* 154:604–612 (1966)). Many aspects of tissue development rely on cell death for the selection of proper sets of cells. For example, in vertebrates, massive numbers of neurons generated in early development become eliminated in late stage refinement of connections (Hamburger et al., *J. Exp. Zool.* 111:457–502 (1949); Oppenheim, *Ann. Rev. Neurosci.* 14:453–501 (1991)). The mechanism is thought primarily to occur through competition for trophic agents derived from target tissues, which may reinforce appropriate patterns of innervation. Similarly, in the immune system, progenitor cells must generate a great diversity of cell types. The differentiation process relies heavily on regulated cell death to eliminate large numbers of cells of inappropriate reactivity (Fesus, *Immunol. Lett.* 30:277–282 (1991); Goldstein et al., *Immunol. Rev.* 121:29–65 (1991)).

The mechanisms and regulation of programmed cell death have a number of implications. For example, the regulation of programmed cell death has implications for oncogenesis (Williams, *Cell* 65 1097–1098 (1991)), immune disease (Ameisen et al., *Immunol. Today* 12:102–105 (1991); Meyaard et al., *Science* 257:217–219 (1992)), and conditions where excessive cell death results in tissue damage, such as neural injury (Choi, *Neuron* 1:623–634 (1988)). Neural and immune system development also display important programmed cell death events. In insects, some cell death is observed early, during neuroblast delamination in the formation of the ventral nerve cord (Doe et al., *Dev. Biol.* 111:193–205 (1985); Jimenez and Campos-Ortega, *Neuron* 5:81–89 (1990)). In vertebrates, cell death that is not associated with target innervation is observed in the spinal ganglia (Hamburger et al., supra; Pannese, *Neuropathol. Appl. Neurobiol.* 2:247–267 (1976); Hamburger et al., *J. Neurosci.* 1:60–71 (1981); Carr et al., *Dev. Brain Res.* 2:157–162 (1982)). Administration in vivo of nerve growth factor prevents nerve cell death (Hamburger et al., supra), suggesting that competition for factors may participate in the selection of neural cells even at early developmental stages. Progenitor cells of the oligodendrocyte lineage also require certain levels of survival factors during early development (Barres et al., *Cell* 70:31–46 (1992)). The types of factors that influence cell survival may change as the cells mature (Barres et al., supra), suggesting that different signals may be involved in the selection of cells at different developmental stages. In the immune system, the elimination of cells through cell death functions at multiple stages. T cell maturation may involve two types of selection processes. Cells lacking appropriate receptors fail to be positively selected for further differentiation and are eliminated (Sha et al., *Nature* 336:73–76 (1988); Teh et al., *Nature* 335:229–233 (1988)). Cells that do develop receptors but are self-reactive are also eliminated (Kappler et al., *Nature* 332:35–40 (1988); MacDonald et al., *Nature* 332:40–45 (1988); Smith et al., *Nature* 337:181–184 (1989). Regulated cell death thus appears to function together with selection to sculpt an appropriate repertoire of cells.

Programmed cell death typically occurs in conjunction with critical differentiation events. Recent work suggests that programmed cell death is a default fate that will occur unless actively inhibited (Barres et al., supra; Raff, *Nature* 356:397–400 (1992). In addition, studies done in *C. elegans* imply that the differentiation pathway and the cell death pathway may be uncoupled genetically (Ellis et al., *Cell* 44:817–829 (1986); Hengartner et al., *Nature* 356:495–499 (1992). Genes that function in the cell death pathway have been identified, such as the ced genes of *Caenorhabditis elegans* (Ellis et al., supra; Hengartner et al., supra). However, genes are also needed to determine when during development that pathway is activated. To coordinate differentiation and death, the activities of genes involved in select differentiation events presumably impinge on control of genes of the death pathway to repress the suicide of appropriate cells.

The Drosophila eye is an excellent genetic system for approaching the problem of how differentiation events and cell death interplay to achieve proper cellular development (Ready, *Trends Neurosci.* 12:102–110 (1989); Banerjee et al., *Neuron* 4:177–187 (1990); Rubin, *Trends Genet.* 7:372–377 (1991)). The adult eye is composed of some 800 repeated neural units called ommatidia, each containing cell types that include three photoreceptor classes, three kinds of pigment cells, cone cells, and a bristle cell complete with socket, neuron, and glial sheath. During the third larval instar, progenitor cells commence differentiation to generate the various cell types (Waddington et al., *Proc. Roy. Soc. Lond.* (B) 153:155–178 (1960)). Differentiation is marked by a morphogenetic furrow that moves from posterior to anterior across the field of progenitor cells in the eye portion of the eye-antennal imaginal disc (Ready et al., *Dev. Biol.* 53:217–240 (1976)). Anterior to the morphogenetic furrow, the progenitor cells undergo division to generate an epithelial field for the differentiation events that commence with the furrow. Thus, at a given time, the disc displays a time line of development, the earliest morphologically evident differentiation events being associated with the furrow. Later events occur toward the posterior of the disc, where a pattern emerges of developing cell clusters. Little is known about the events before furrow formation that lead to differentiation, although cell competence, hormones, and possibly inductive interactions appear to be involved (Bodenstein, *Postembryotic Development*, in *Insect Physiology*, K. D. Roeder, ed. New York, Wiley & Sons, Inc. pp 822–865 (1953); White, *J. Exp. Zool.* 148:223–239 (1961); Gateff et al., *Roux's Arch. Dev. Biol.* 176:171–189 (1975). Some cell death is a normal part of the developmental process, having been observed in the eye disc during morphogenesis (Fristrom, *Mol. Gen. Genet.* 103:363–379 (1969); Spreij, *Neth. J. Zool.* 21:221–264 (1971); Wolff et al., *Development* 113:825–839 (1991)).

One mutation, eya, has proven useful in the study of eye development. Flies with the eya[1] mutation show remarkable specificity for loss of the adult compound eyes (FIGS. 1A and 1B; Sved, *Dros Inf. Serv.* 63:169 (1986); Renfranz et al., *Dev. Biol.* 136:411–429 (1989)). All other external structures appear normal, including the adult ocelli, which develop from edges of the eye imaginal discs. In the brain, there is loss of the first optic ganglion (lamina) and reduction in size of the second optic ganglion (medulla), and the lobula and lobula plate show some disorganization (FIGS. 1C and 1D). These brain defects are similar to those observed in other eyeless mutants and are consistent with the influence of retinal neurons on development of the optic lobes (Power, *J. Exp. Zool.* 94:33–71 (1943); Meyerowitz et al., *Dev. Biol.* 62:112–142 (1978); Fischbach, *Dev. Biol.* 91:1–18 (1983); Selleck et al., *Neuron* 6:83–99 (1991).

In normal development, eye differentiation begins during the third instar larval stage when the morphogenetic furrow sweeps from posterior to anterior across the eye portion of the eye-antennal disc, leaving clusters of differentiating photoreceptor neurons in its wake (Ready et al., supra). The differentiating clusters can be visualized by staining with monoclonal antibodies, such as neuronspecific MAb 22C10 (FIG. 2E; Zipursky et al., *Cell* 36:15–26 (1984)). In $eya^1$ eye discs, the normal expansion of the eye portion of the disc during the third instar larval stage is arrested, and no furrow forms (FIGS. 2S, 2D, and 2F). When stained with antibodies that normally highlight the differentiating neurons, the mutant eye discs fail to show any evidence of cluster formation (FIG. 2F; also Renfranz et al., supra). In contrast, the antenna portion of the disc expands and differentiates normally. The larval photoreceptor organ also appears normal, and Bolwig's nerve from the larval visual organ (Bolwig, *Vidensk. Medd. fra. Dansk. Naturh. Foren. Bd.* 109:80–212 (1946) traverses the eye disc in its path into the optic stalk, as in a normal disc. The $eya^1$ mutation thus appears to affect specifically the progenitor cells that normally form the adult compound eye.

In addition, the study of genes that function in the fly eye has provided insight into the developmental roles of many proteins homologous to human genes (Greenwald et al., *Cell* 68:271–281 (1992). Anophthalmia, or the lack of eyes, occurs in many organisms, including humans (Apple et al., *Ocular Pathology: Clinical applications and Self-Assessment*, St. Louis, Mosby-Year Book, Inc. (1991)). In a striking example, congenital aniridia in humans resembles the Small eye mutation of mouse (Glaser et al., *Science* 250:823–827 (1990), van der Meer-de Jong et al., *Genomics* 7:270–275 (1990); both result from mutations of genes that are homologous (Hill et al, *Nature* 354:522–525 (1991); Ton et al., *Cell* 67:1059–1074 (1991); Jordan et al., *Nature Genet.* 1:328–332 (1992)).

SUMMARY OF THE INVENTION

It is an object of the invention to provide programmed cell death antagonist (PCDA) proteins, and variants thereof, and to produce useful quantities of these PCDA proteins using recombinant DNA techniques.

It is a further object of the invention to provide recombinant nucleic acids encoding PCDA proteins, and expression vectors and host cells containing the nucleic acid encoding the PCDA protein.

An additional object of the invention is to provide methods for producing the PCDA protein, and for regulating the programmed cell death of an organism.

In accordance with the foregoing objects, the present invention provides recombinant PCDA proteins, and isolated or recombinant nucleic acids which encode the PCDA proteins of the present invention. Also provided are expression vectors which comprise DNA encoding a PCDA protein operably linked to transcriptional and translational regulatory DNA, and host cells which contain the expression vectors.

An additional aspect of the present invention provides methods for producing PCDA proteins which comprises culturing a host cell transformed with an expression vector and causing expression of the nucleic acid encoding the PCDA protein to produce a recombinant PCDA protein.

Additionally provided are methods of regulating the programmed cell death of a population of cells in an organism.

BRIEF DESCRIPTION OF THE DRAWINGS

FIG. 1(A–D) depicts the adult phenotype of $eya^1$ flies. Scanning electron micrographs of normal (A) and $eya^1$ mutant (B) heads. The compound eyes are missing entirely in $eya^1$ flies. The three dorsal ocelli and other external head structures are present. Silver-stained horizontal sections of a normal fly brain (C) and $eya^2$ mutant fly brain (D). In the mutant, the retina (r) and lamina (l) are completely missing, the medulla (m) appears reduced in size, and the lobula (lo) and lobula plate (lp) are less organized that normal.

FIG. 2(A–F) depicts the phenotype of $eya^1$ in the developing eye disc. (A and B) depict eye-antennal discs from early third instar larvae, stained with neuron specific MAb22C10. The furrow is not yet present; no clusters have formed. The eye portion (e) of the $eya^1$ disc appears normal in size at this stage. Bolwig's nerve, which stains with MAb22C10, transverses the discs. (C and D) depict slightly older discs from early third instar larvae. The eye portion (e) of the $eya^1$ disc is still expanding. (E) depicts the wild-type-eye-antennal disc from a late (crawling) third instar larva stained with MAB22C10. The morphogenic furrow (f) is halfway across the eye portion (e) of the disc. The developing neuronal clusters posterior to the furrow are highlighted by the antibody staining. (F) depicts the $eya^1$ mutant eye-antennal disc from a late (crawling) third instar larva stained with MAb22C10. The antennal portion (a) of the disc has expanded normally, but the eye portion (e) of the disc is much smaller than normal. No furrow is formed; neural clusters fail to develop, illustrated by the lack of staining with MAb22C10. Bolwig's nerve is present. Bar= 50 µm.

FIG. 3(A–H) depicts compound eye phenotypes of flies expressing various alleles of eya. (A–D) are scanning electron micrographs. (E–H) are tangential sections, anterior to the right. (A) and (E) are wild type flies. The regular ommatidial pattern is shown by the arrow in (E). The rhabdomeres of seven photoreceptor cells are visible: six outer, and inner seventh. The rhabdomere of the eighth photoreceptor is beneath that of the seventh. The photoreceptor cells are surrounded by a pigmented lattice. (B) and (F) are mild allele $eya^{E3}$ heterozygous with $eya^1$. The eye is slightly reduced and rough. Photoreceptor cells are occasionally missing (arrow in F) and the pigmented lattice is less regular than in wild type. Many ommatidia appear normal (white arrow in (F)). (C) and (G) are intermediate allele $eya^{E4}$ heterozygous with $eya^1$. The eye is reduced and rough. Many ommatidia contain the full complement of photoreceptor cells (white arrow in (G)), although cells are sometimes missing (black arrow) and the pigmented lattice is less organized than in wild type. (D) and (H) are severe allele $eya^{E1}$ heterozygous with $eya^1$. In flies expressing this allelic combination, the eye is greatly reduced and rough (D), or missing altogether. Although the ommatidial pattern of such severely reduced eyes shows disorganization (H), many ommatidia contain all the photoreceptor cell types (white arrows) and the pigmented lattice is present.

FIG. 4(A–H) depicts the eye disc phenotypes of larvae expressing various alleles of eya. Eye portions of eye-antennal discs from crawling third instar larvae. (A–D) depict MAB 22C10 staining, which highlights neural clusters. (E–H) depicts acridine orange staining, which highlights dead cells. Arrows mark the morphogenic furrow. (A and E) are wild type. (A) posterior to the furrow clusters are developing. (E) dead cells appear as bright dots of fluorescence. A small amount of cell death occurs in a band just anterior to the furrow. (B and F) are mild allele eya$^{E3}$ heterozygous with eya$^1$. (B) Many neural clusters form, consistent with the only slightly reduced eye in the adult (see FIG. 3B). (F) Anterior to the furrow (arrow), an increase in the amount of cell death occurs, highlighted by acridine orange staining. The increased cell death occurs in the same region of the disc just anterior to the furrow where normally some cell death occurs. (C and G) are intermediate allele eya$^{E4}$ heterozygous with eya$^1$. (C) Fewer clusters form. Anterior to the furrow, condensed and refractile dying cells are visible. (G) Acridine orange highlights the increased degeneration that occurs in a broad band anterior to the furrow (arrows). (D and H) are severe allele eya$^{E1}$ heterozygous with eya$^1$. (D) Many fewer clusters form in the eye disc. Anterior to the furrow, condensed dead cells are visible. Inset: higher magnification view of condensed and refractile bodies anterior to the furrow. Arrows highlight a few examples. (H) Acridine orange staining highlights the great increase in cell death that occurs anterior to the furrow in the disc. Bars are 50 μm.

FIG. 5(A–B) depicts the cell death in an eye disc of an eya mutant that forms a reduced eye. (A) eye portion of an eye-antennal disc from a third instar larva expressing an intermediate allele eya$^{E9}$ heterozygous with eya$^1$. Anterior to the furrow (arrow) cell death is seen in the basal region of the disc (boxed area). Dead cells fragment into electron-dense bodies; these appear to become engulfed by surrounding cells. Posterior to the furrow, where the clusters are differentiating, no cell death is seen. (B) Higher magnification view from the box in (A). Within dead cell fragments, intact cellular organelles may be seen (arrow points toward what appears to be a nucleus). Also visible are fragments of dead cells within other cells. Bar in (A)=10 μm, bar in (B)=2 μm. Anterior to the right.

FIG. 6(A–C) depicts the molecular analysis of the eya chromosomal region. (A) shows the molecular organization of the eya region. The restriction map from overlapping cosmid and phage clones shows Not1 (N), BamH1 (B), EcoR1 (E), Sal1 (S), and Xba1 (X) sites. This region resides in cytological region 26E on chromosome 2. Above the restriction map are indicated the DNA restriction fragments within which the breakpoints of six X-ray-induced alleles fall. Also shown is the location of the breakpoint of an X-ray allele of dpp, T(2;3)DTD46, that has one breakpoint in 26E and that fails to complement eya mutations. Illustrated below the restriction map are the intron-exon structures of prototypes of the two classes of cDNA that span the region. The start (ATG) and stop (TGA) codons correspond to those of the longest potential open reading frames. The initiation sites of transcription have not been determined. (B) Northern blot analysis. Northern blot of poly(A)+RNA isolated from wild-type embryos (0–24 hours), adult bodies and heads, and adult heads of the eya$^1$ mutant. Each lane has 7.5 μg of RNA. The blot was probed with the Not1-EcoR1 restriction fragment indicated by an asterisk on the restriction map in (A). A transcription unit of 3.5 kb is detectable in embryos and adult heads; its intensity is reduced in the heads of the eya$^1$ mutant. (C) is a Northern blot of eye disc poly(A)+RNA, isolated from 200 mid-third instar larval eye-antennal discs from wild type and the eya$^1$ mutant, probed with the entire type 1 cDNA. A transcript of 3.5 kb is detectable in the wild type, but is missing in the mutant.

FIGS. 7(A-1 to A-7) and B) depict the nucleic acid and protein sequence of the eya gene. (A-1 to A-7) is the nucleic acid sequence (SEQ ID NO:1) of the type 1 cDNA, with the start and stop of the coding region shown and the corresponding amino acid sequence (SEQ ID NO:2). (B) is N-terminus of the type II cDNA (SEQ ID NO:3), and the corresponding amino acid sequence (SEQ ID NO:4). For the type I cDNA, the sequence at the proposed start site has a 2/4 bp match with the Drosophila translation initional consensus (Cavener, Nucl. Acids. Res. 15:1353–1361 (1987). For the type II cDNA, the match is 3/4 bp. The first 19 amino acids of the type I cDNA and the first 25 of the type II are generated by alternative splicing. Within the amino acid sequence common to both cDNA classes, three charged clusters (Brendel et al., Proc. Natl. Acad. Sci. USA 89:2002–2006, 1992) are arranged as a basic stretch (solid underline), an acidic stretch (double underline), then a second basic stretch (solid underline). Five regions (amino acids 83–203,236–256, 409–429, 489–509, and 671–691) are predicted to be hydrophobic β-helical regions by the algorithm of Eisenberg et al., J. Mol. Biol. 179:125–142 (1984). The opa repeat spans amino acids 40–62. A possible PEST protein degradation sequence (Rogers et al., Science 234:364–368 (1986); Rechsteiner, Sem. Cell Biol. 1:433–440 (1990)) is underlined with a dashed line, and potential cyclic nucleotide-dependent, protein kinase C and tyrosine kinase phosphorylation sites are circled. Amino acids 18–23 are a candidate for a nuclear localization signal (Chelsky et al., Mol. Cell. Biol. 9:2487–2492 (1989)). The 3' untranslated region is approximately 500 nt and has two AATAAA sites (boxed) that could serve as polyadenylation signal sequences. Within the 3' tail region are sit ATTTA repeats (underlined), which are found in the 3' untranslated regions of dynamically expressed genes and are implicated in rapid message turnover (Shaw et al., Cell 46:659–667 (1986)). The intron sites (carets) were determined by comparing the genomic sequence with that of the cDNAs.

FIG. 8(A–G) depicts the protein and transcript expression of the eya gene in eye discs. (A–E) are eye discs stained with a mouse polyclonal antiserum directed against the eya protein. (F–G) are transcript expression using digoxigenin labeling of the type I cDNA. (A and B) show that protein expression begins during the second instar, remains on prior to furrow formation in third instar, and appears graded with expression stronger in the posterior region of the disc than the anterior. Two eye discs are visible in (A). (C and D) As the furrow forms and progresses across the disc, expression remains strong in the region just anterior to the furrow (arrows). The protein is expressed more weakly in the anterior of the eye portion of the disc. Posterior to the furrow, expression continues. (E) Longitudinal section of a late third instar eye disc stained with the polyclonal antiserum, detected with a secondary antibody conjugated to horseradish peroxidase. Onset of expression is anterior to the furrow (arrow). The protein is localized to nuclei. (F) Longitudinal section of a late third instar eye disc labeled by in situ hybridization. Dark-field image superimposed on a bright-field image. Onset of transcript signal (white dots) is in the region anterior to the furrow (arrow), and continues posterior to the furrow, wherein it is expressed primarily in the basal region. (G) In situ expression in a whole-mount preparation of an eye disc from a wild type crawling third instar larva. One flap of the disc is curled over at the bottom (outlined with dashes). Transcript expression begins anterior to the furrow (arrow), and is weaker in the posterior region of the disc. Bar (A–D and G)=50 μm. Bar in (E) and (F) is 20 μm.

FIG. 9(A–F) depicts the restoration of development of the eye in eya mutants through expression of the hsp-eya minigene by heat shock. (A–C) are scanning electron micrographs. (D–E) are tangential sections of the eye. (A and D) are the wild-type eye and ommatidial pattern. (B) eya² mutant harboring an hsp-eya minigene insert, raised without heat shock. The mutant is completely eyeless. (C and E) eya² mutant bearing an hsp-eya minigene insert, heat pulsed during the larval stages of development. Both the external eye morphology and the internal ommatidia are restored. Anterior to the right.

DETAILED DESCRIPTION OF THE INVENTION

The present invention provides novel PCDA proteins. As used herein, a "PCDA protein" is a protein which exhibits a repressive or antagonistic effect on programmed cell death. That is, a population of cells which otherwise would undergo programmed cell death are prevented from dying by the presence of the PCDA protein. It is to be understood that the precise mechanism of the regulatory action of the PCDA protein is not known, although three possible mechanisms are proposed. The PCDA protein may repress cell death, thus allowing cells to enter the differentiation pathway; the PCDA protein may promote differentiation, which represses cell death; or the PCDA protein both promotes differentiation and represses cell death.

The PCDA proteins and the nucleic acid encoding the PCDA proteins of the present invention are homologous to the Drosophila amino acid and nucleic acid sequence shown in FIG. 7, as outlined below, and it is this homology which serves as the major distinguishing characteristic of a PCDA protein. In addition, a PCDA protein may have one or more of the following characteristics. First, the PCDA proteins are localized in the nucleus. In addition, the expression of PCDA protein at certain times in the development and differentiation pathway will prevent the programmed cell death of a population of cells. Alternatively, the repression or inhibition of the PCDA protein may expedite the programmed cell death of a cell population.

Accordingly, the PCDA proteins of the present invention find use in a number of applications. For example, PCDA proteins are useful as reagents in diagnostic assays for the presence of PCDA protein or antibodies to PCDA protein, or when insolubilized in accord with known methods as agents for the purification of PCDA protein antibodies from antisera or hybridoma culture. PCDA proteins are also useful as an immunogen or hapten to produce antibodies to PCDA protein. These antibodies are useful in the diagnostic assay of PCDA protein and elucidation of the localization of the PCDA protein within a tissue or organism.

At the broadest level, the PCDA proteins of the present invention are useful as regulators or modulators of programmed cell death. Thus the expression of the nucleic acid encoding PCDA protein, or the addition of the PCDA protein directly, prevents programmed cell death in a cell population. Conversely, the inhibition of a PCDA protein is useful in cell populations in which cell death is desirable, for example in tumor cells. Accordingly, inhibitors such as antisense nucleic acids encoding PCDA protein of the present invention are useful.

The nucleic acids of the present invention which encode PCDA proteins are also useful in the generation of transgenic animals, used as models for the elucidation of programmed cell death function and effect. For example, transgenic animals which do not contain a functional PCDA protein gene are useful in the determination of the role of programmed cell death in development. These transgenic animals are also useful as cancer models, since many types of cancer exhibit a loss of cellular programmed cell death, with a corresponding increase in cancerous cellular growth and proliferation. Transgenic animals with increased production of the PCDA protein are also useful.

The nucleic acids of the present invention are also useful in gene therapy, wherein nucleic acid is targeted to a cell type or tissue to prevent cell death. This includes both the addition of a PCDA protein gene or the deletion of a PCDA protein gene.

In accordance with the above applications, the PCDA proteins and nucleic acids are defined and generated as outlined below in detail.

The present invention provides novel PCDA proteins. A PCDA protein nucleic acid or PCDA protein is initially identified by substantial nucleic acid and/or amino acid sequence homology to the sequences shown in FIGS. 7A and 7B (SEQ ID NOS:1–4). Such homology can be based upon the overall nucleic acid or amino acid sequence.

In the case of the protein, the overall homology of the protein sequence to the amino acid sequence shown in FIG. 7 (SEQ ID NOS:7 and 4) is preferably greater than about 40%, more preferably greater than about 60% and most preferably greater than 80%. In some embodiments the homology will be as high as about 90 to 95 or 98%. This homology will be determined using standard techniques known in the art, such as the Best Fit sequence program described by Devereux et al., Nucl. Acid Res. 12:387–395 (1984). The alignment may include the introduction of gaps in the sequences to be aligned. In addition, for sequences which contain either more or fewer amino acids than the protein shown in FIG. 7 (SEQ ID NOS:7 and 4), it is understood that the percentage of homology will be determined based on the number of homologous amino acids in relation to the total number of amino acids. Thus, for example, homology of sequences shorter than that shown in FIG. 7 (SEQ ID NOS:2 and 4) will be determined using the number of amino acids in the shorter sequence.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Thus the homology of the nucleic acid sequence as compared to the nucleic acid sequence of FIG. 7 (SEQ ID NOS:1 and 3) is preferably greater than 40%, more preferably greater than about 60% and most preferably greater than 80%. In some embodiments the homology will be as high as about 90 to 95 or 98%.

cDNA analysis of the PCDA protein from Drosophila reveals that at least two separate cDNAs exist, the putative result of alternate splicing. These cDNAs, type I and type II, differ in the use of 5' exons (FIG. 6A). Accordingly, PCDA proteins may exhibit N-terminal heterogeneity and truncation.

The PCDA proteins and nucleic acids of the present invention are recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Specifically included within the definition of nucleic acid are anti-sense nucleic acids. An anti-sense nucleic acid will hybridize to the nucleic acid sequence shown in FIG. 7 (SEQ ID NOS:1 and 2), but may contain ribonucleotides as well as deoxyribonucleotides. Generally, anti-sense nucleic acids function to prevent expression of mRNA, such that a PCDA protein is not made. The nucleic acid may have introns which are not transcribed, in the case of genomic DNA, for example. The nucleic acid may be double stranded, single stranded, or contain portions of both double stranded or single stranded sequence. By the term "recombinant nucleic acid" herein is meant nucleic acid, originally formed in vitro by the manipulation of nucleic acid by endonucleases, in a form not normally found in nature. Thus an isolated PCDA protein gene, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host. The definition includes the production of a PCDA protein from one organism in a different organism or host cell. Alternatively, the protein may be made at a significantly higher concentration than is normally seen, through the use of a inducible promoter or high expression promoter, such that increased levels of the protein is made. Additionally, the protein may be made at a different stage in development than normal or as a result of new experimental conditions, through the use of a temperature sensitive or heat shock promoter. Alternatively, the protein may be in a form not normally found in nature, as in the addition of an epitope tag or amino acid substitutions, insertions and deletions.

Also included with the definition of PCDA protein are PCDA proteins from other organisms, which are cloned and expressed as outlined below.

A PCDA protein nucleic acid from an organism other than Drosophila can be readily identified by standard methods utilizing all or part of the sequence shown in FIG. 7 (SEQ ID NOS:1 and 3). For example, labelled probes corresponding to the sequence of FIG. 7 (SEQ ID NOS:1 and 3) can be used for hybridization to detect the presence of an PCDA protein gene in a particular organism. In addition, such probes can be used to screen genomic or cDNA libraries or to identify one or more bands containing all or part of the PCDA protein gene by hybridization to an electrophoretically separated preparation of genomic DNA digested with one or more restriction endonucleases.

The length of the probes will vary depending upon the organism screened and the amount of expected homology. Generally probes may be at least about 10 bases in length, and will generally be no more than about 50 bases in length, with a preferred range of about 15 to 30 bases. However, it is to be understood that much longer probes may be used, comprising all or a significant part of the sequence shown in FIG. 7 (SEQ ID NOS:1 and 3), for example to clone the Drosophila protein.

The hybridization conditions will vary depending upon the probe used, and will be ascertainable by one skilled in the art using routine experimentation. Generally, low stringency conditions, e.g. 4–5× SSC at 50° C., will be used in the initial screening of genomes other than that of Drosophila. High stringency conditions may also be used, i.e. 0.1× SSC at 65° C., when greater homology is expected. Accordingly, nucleic acids which hybridize, under either low or high stringency conditions, to the sequence shown in FIG. 7 (SEQ ID NOS:1 and 3) are within the scope of the invention.

In the case of anti-sense nucleic acids, an anti-sense nucleic acid is defined as one which will hybridize to all or part of the sequence shown in FIG. 7 (SEQ ID NOS:1 and 3). Generally, the hybridization conditions used for the determination of anti-sense hybridization will be high stringency conditions, such as 0.1× SSC at 65° C.

Once the PCDA protein nucleic acid is identified, it can be cloned and, if necessary, its constituent parts recombined to form the entire PCDA protein nucleic acid. Once isolated from its natural source, e.g., contained within a plasmid or other vector or excised therefrom as a linear nucleic acid segment, the recombinant PCDA protein nucleic acid can be further used as a probe to identify and isolate other PCDA protein nucleic acids. It can also be used as a "precursor" nucleic acid to make modified or variant PCDA protein nucleic acids and proteins.

Using the nucleic acids of the present invention which encode PCDA protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the PCDA protein. "Operably linked" in this context means that the transcriptional and translational regulatory DNA is positioned relative to the coding sequence of the PCDA protein in such a manner that transcription is initiated. Generally, this will mean that the promoter and transcriptional initiation or start sequences are positioned 5' to the PCDA protein coding region. The transcriptional and translational regulatory nucleic acid will generally be appropriate to the host cell used to express the PCDA protein; for example, transcriptional and translational regulatory nucleic acid sequences from Drosophila will be used to express the PCDA protein in Drosophila. Numerous types of appropriate expression vectors, and suitable regulatory sequences are known in the art for a variety of host cells.

In general, the transcriptional and translational regulatory sequences may include, but are not limited to, promoter sequences, leader or signal sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The PCDA proteins of the present invention are produced by culturing a host cell transformed with an expression vector containing nucleic acid encoding a PCDA protein, under the appropriate conditions to induce or cause expression of the PCDA protein. The conditions appropriate for PCDA protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

A recombinant PCDA protein may be expressed intracellularly or secreted. The PCDA protein may also be made as a fusion protein, using techniques well known in the art.

In a preferred embodiment, the PCDA protein is purified or isolated after expression. The PCDA proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the PCDA protein may be purified using a standard antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the PCDA protein. In some instances no purification will be necessary.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli*, *Bacillus subtilis*, SF9 cells, C129 cells, 293 cells, Neurospora, BHK, CHO, COS, and HeLa cells, immortalized mammalian myeloid and lymphoid cell lines.

In a preferred embodiment, PCDA proteins are produced in insect cells. Expression vectors for the transformation of insect cells, and in particular, baculovirus-based expression vectors, are well known in the art. Briefly, baculovirus is a very large DNA virus which produces its coat protein at very high levels. Due to the size of the baculoviral genome, exogenous genes must be placed in the viral genome by recombination. Accordingly, the components of the expression system include: a transfer vector, usually a bacterial plasmid, which contains both a fragment of the baculovirus genome, and a convenient restriction site for insertion of the PCDA protein; a wild type baculovirus with a sequence homologous to the baculovirus-specific fragment in the transfer vector (this allows for the homologous recombination of the heterologous gene into the baculovirus genome); and appropriate insect host cells and growth media.

After inserting the nucleic acid encoding the PCDA protein into the transfer vector, the vector and the wild type viral genome are transfected, usually through co-transfection, into an insect host cell where the vector and viral genome are allowed to recombine. Methods for introducing heterologous DNA into the desired site in the baculovirus are known in the art. For example, a preferred embodiment uses an insertion into the polyhedrin gene, such that recombination results in a loss of the polyhedrin protein. Then the insertion proceeds via homologous double recombination. Homologous recombination generally occurs at low frequency (between 1% and about 5%). Thus, the majority of the virus produced after cotransfection is wild-type. However, due to the very high levels of polyhedrin production by the native virus, the wild-type accumulated polyhedrin protein forms highly refractile occlusion bodies that are readily visualized under a light microscope. Therefore, cells infected with recombinant viruses which insert into the polyhedrin gene lack occlusion bodies, making visualization of recombinants with a light microscope possible.

Materials and methods for baculovirus/insect cell expression systems are commercially available in kit form; for example the "MaxBac" kit from Invitrogen in San Diego. Baculovirus transfer vectors usually contain a baculovirus promoter. A baculovirus promoter is any DNA sequence capable of binding a baculovirus RNA polymerase and initiating the downstream (5' to 3') transcription of a coding sequence, i.e. the PCDA protein gene, into mRNA. Of particular use as promoters are the promoters from the genes encoding the viral polyhedrin protein and the p10 protein.

A signal sequence may also be included in the insect cell expression vector. These signal sequences can be derived from secreted insect or baculovirus proteins, such as the polyhedrin gene. Alternatively, since the signals for mammalian cell post-translational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin may be used.

Mammalian expression systems are also known in the art and are used in one embodiment. A mammalian promoter is any DNA sequence capable of binding mammalian RNA polymerase and initiating the downstream (3') transcription of a coding sequence for PCDA protein into mRNA. A promoter will have a transcription initiating region, which is usually place proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element, typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, and herpes simplex virus promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived form SV40.

Some genes may be expressed more efficiently when introns are present. Several cDNAs, however, have been efficiently expressed from vectors that lack splicing signals. Thus, in some embodiments, the nucleic acid encoding the PCDA protein includes introns.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, encapsulation of the polynucleotide (s) in liposomes, and direct microinjection of the DNA into nuclei.

In a preferred embodiment, PCDA protein is produced in yeast cells. Yeast expression systems are well known in the art, and include expression vectors for Saccharomyces cerevisiae, Candida albicans and C. maltosa, Hansenula polymorpha, Kluyveromyces fragilis and K. lactis, Pichia guillerimondii and P. pastoris, Schizosaccharomyces pombe, and Yarrowia lipolytica. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the G418 resistance gene, which confers resistance to G418; and the CUP1 gene, which allows yeast to grow in the presence of copper ions.

Once expressed and purified if necessary, the PCDA proteins, as well as the PCDA protein nucleic acids as outlined below, may be administered to an animal or organism to regulate programmed cell death in a cell population. By "regulating programmed cell death" or "modulating programmed cell death" or grammatical equivalents herein is meant the alteration of a pattern of programmed cell death. Generally, this regulation will be the repression or prevention of programmed cell death, such that a cell population slated to undergo programmed cell death is prevented from doing so, resulting in the retention of a viable cell population. The regulation of programmed cell death does not require that the complete population are prevented from dying, but that some subset of the population is prevented.

By "cell population" or "a population of cells" or grammatical equivalents herein is meant a collection of cells, generally related developmentally or as cells of a tissue. For example, progenitor cells of a certain type may be considered a cell population, or eye tissue cells. In a preferred embodiment, the cell population which is prevented from undergoing programmed cell death is the progenitor eye cells.

The administration of the PCDA protein is done in a variety of ways. Generally, the PCDA proteins of the present invention can be formulated according to known methods to prepare pharmaceutically useful compositions, whereby the PCDA protein is combined in admixture with a pharmaceutically acceptable carrier vehicle. Suitable vehicles and their formulation are well known in the art. Such compositions will contain an effective amount of the PCDA protein together with a suitable amount of vehicle in order to prepare pharmaceutically acceptable compositions for effective administration to the host. The composition may include salts, buffers, carrier proteins such as serum albumin, targeting molecules to localize the PCDA protein at the appropriate site or tissue within the organism, and other molecules.

In a preferred embodiment, the PCDA protein is administered in vivo to a developing organism to prevent anophthalmia or aniridia. This administration may be accomplished either through the administration of the PCDA protein itself, or through the administration, by gene therapy, of nucleic acid encoding the PCDA protein, resulting in the in vivo expression of the protein. For example, the expression of the PCDA protein gene after microinjection into eyeless Drosophila mutant embryos allows the formation of eyes, due to the prevention of the programmed cell death of the eye progenitor cells.

Also contemplated within the scope of the invention is the use of inhibitors or repressors of the PCDA protein to increase programmed cell death. For example, the use of an inhibitor of PCDA protein in certain tumor cells can allow the repression of cell death to be avoided, thus resulting in the elimination of the tumor through cell death. This inhibitor may be an anti-sense nucleic acid, for example, or an antibody. The anti-sense nucleic acid will be all or part of the nucleic acid complement of the coding nucleic acid shown in FIG. 7 (SEQ ID NOS:1 and 3). The creation and administration of anti-sense nucleic acids is known in the art.

In a preferred embodiment, as noted above, expression of the PCDA protein occurs as a result of gene therapy, that is, the administration of nucleic acid encoding a PCDA protein to an organism. Thus, the PCDA protein will be produced endogenously in the organism, rather than administered in a protein form. The gene therapy may be done at an embryonic stage of the organism, such that the germ cells of the organism contain the PCDA protein nucleic acid, resulting in a transgenic organism, or at a later stage of development to specific somatic cells, such that only a particular tissue or portion of a tissue contains the PCDA protein nucleic acid. Techniques for gene therapy are well known in the art, as are the techniques for the creation of transgenic organisms. By the term "transgenic organism" herein is meant transgenic animals, such as mammals, as well as insects.

It is to be understood that the administration of a PCDA protein nucleic acid in gene therapy may take several forms, all of which are included in the scope of the present invention. The nucleic acid encoding a PCDA protein may be administered in such a manner as to add the PCDA protein nucleic acid to the genome of the cell or the organism. For example, administering a nucleic acid encoding a PCDA protein, under the control of a promoter which results in an increase over background expression of PCDA protein, results in the incorporation of the nucleic acid into the genome of the cell or the organism, such that increased levels of PCDA protein are made. For example, this may be done to a cell population which is slated to undergo an undesirable level of programmed cell death, to preserve the cells. Alternatively, an anti-sense nucleic acid encoding a PCDA protein, that is, a nucleic acid which will hybridize to all or part of the coding strand for the PCDA protein, may be administered to decrease the amount of PCDA protein expressed in a cell population. Optionally, a nucleic acid encoding a PCDA protein may be used to delete the gene from the cell or organism, resulting in a decrease in the amount of PCDA protein made by the cell. This may be done, for example, to a population of cancer cells to derepress programmed cell death. Techniques for the creation of deletion mutants is well known in the art.

Construction of appropriate expression vehicles and vectors for gene therapy applications will depend on the organism to be treated and the purpose of the gene therapy. The selection of appropriate promoters and other regulatory DNA will proceed according to known principles, based on a variety of known gene therapy techniques. For example, retroviral mediated gene transfer is a very effective method for gene therapy, as systems utilizing packaging defective viruses allow the production of recombinants which are infectious only once, thus avoiding the introduction of wild-type virus into an organism. Alternative methodologies for gene therapy include non-viral transfer methods, such as calcium phosphate co-precipitation, mechanical techniques, for example microinjection, membrane fusion-mediated transfer via liposomes, as well as direct DNA uptake and receptor-mediated DNA transfer.

Also included within the definition of PCDA proteins of the present invention are amino acid sequence variants. These variants fall into one or more of three classes: substitutional, insertional or deletional variants. These variants ordinarily are prepared by site specific mutagenesis of nucleotides in the DNA encoding the PCDA protein, using cassette mutagenesis or other techniques well known in the art, to produce DNA encoding the variant, and thereafter expressing the DNA in recombinant cell culture as outlined above. However, variant PCDA protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the PCDA protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed PCDA protein variants screened for the optimal combination of desired activity. Techniques for making substitution mutations at predetermined sites in DNA having a known sequence are well known, for example, M13 primer mutagenesis. Screening of the mutants is done using assays of PCDA protein activities, as is known by those in the art. For example, nucleic acid encoding the variants may be put under the control of a heat shock promoter and injected into embryos, and heat pulse experiments done to evaluate the effect of the variant PCDA protein on the development of an organism. Alternatively, the variant PCDA protein may be expressed and its biological characteristics evaluated, for example its binding to DNA.

Amino acid substitutions are typically of single residues; insertions usually will be on the order of from about 1 to 20 amino acids, although considerably larger insertions may be tolerated. Deletions range from about 1 to 30 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances.

When small alterations in the characteristics of the PCDA protein are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophobic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity as the naturally-occurring analogue, although variants also are selected to modify the characteristics of the polypeptide as needed. For example, epitope coding sequences may be added or protease recognition sites eliminated, without altering the biological activity of the polypeptide. The evaluation of the new characteristics of the polypeptide will vary with the alteration. For example, the addition of an epitope coding sequence may be evaluated by antibody binding studies, and the deletion of a protease recognition site evaluated by treatment with protease followed by gel electrophoresis or a biological activity assay. Other changes may be evaluated using assays for PCDA protein activities and characteristics, as will be known to those skilled in the art of PCDA proteins. These guidelines allow one skilled in the art to successfully evaluate the effect and characteristics of any insertion, deletion or substitution of amino acid sequence in a PCDA protein.

Alternatively, the variant may be designed such that the biological activity of the PCDA protein is altered. To this end, there are several regions within the protein which may be subjected to amino acid substitutions, deletions or insertions. For example, the PCDA protein from Drosophila exhibits three charged clusters (Brendel, supra) arranged as a basic stretch at amino acids 449 to 471 (unless otherwise noted, all amino acids are numbered according to the type I numbering of FIG. 7, an acidic stretch at amino acids 528 to 563, and a basic stretch at amino acids 600 to 629. Multiple charge clusters such as these are uncommon and are generally associated with regulatory proteins, including protooncogenes, transcription factors, and various types of receptors (Brendel et al., Proc. Natl. Acad. Sci. USA 86:5698–5702 (1989), Karlin et al., Oncogene 5:85–95 (1990)). In addition, the PCDA protein gene from Drosophila contains 5 regions which are predicted to be hydrophobic α-helical regions using the algorithm of Eisenberg, et al., supra. These regions are found at amino acids 83–103, 236–256, 409–429, 489–509, and 671–691. An opa repeat spans amino acids 40–62. A putative PEST protein degradation sequence (Rogers, et al., supra, Rechsteiner, supra) is found at amino acids 373–388. Putative cyclic nucleotide dependent protein kinase C and tyrosine kinase phosphorylation sites are found at Thr447, Thr453, Thr456, Ser615, Ser658, Tyr706, and Thr718. Finally, amino acids 18–23 are a candidate for a nuclear localization signal (Chelsky et al., supra). It is interesting to note that these amino acids span the beginning of the common sequence region. Thus amino acid variants within all these regions are contemplated.

Important functional domains within the protein may also be identified by comparing the amino acid sequence of variants, generated by mutagenesis, with the wild-type gene.

Variants are assayed using the techniques outlined in Example 4, as are known to those skilled in the art. For example, injection of embryos with nucleic acid encoding the variants can result in the integration of the nucleic acid encoding the variant, with a resulting alteration in the phenotype of the organism.

Also included with the definition of PCDA protein for the purposes of the present invention are fragments of PCDA protein or truncated PCDA protein. For example, C- or N-terminal truncations, or both, may be made which retain full or partial biological activity. For example, the alternate splicing seen in the Drosophila melangaster eye suggests that N-terminal truncations are tolerated.

Alternatively, N- or C-terminal truncations, or both, may decrease or eliminate the biological activity of the enzyme. However, variant PCDA proteins which display low or negligible biological activity are included in the definition of PCDA protein if the variant exhibits at least 40% homology with full-length PCDA protein and shares at least one immunological epitope in common with the full-length PCDA protein.

PCDA protein derivatives that are not biologically active but which are capable of cross-reacting with antisera or antibodies to biologically active PCDA protein, as well as biologically active PCDA proteins, are useful in several applications. These derivatives are useful as reagents in diagnostic assays for PCDA protein or antibodies to PCDA protein, or when insolubilized in accord with known methods as agents for the purification of PCDA protein antibodies from antisera or hybridoma culture supernatants. These derivatives are also useful as immunogens to biologically active PCDA protein. In addition, these derivatives are useful in assays of PCDA protein functions, such as assays of binding interactions, for example interactions between a PCDA protein and DNA sequences, and in assays to determine the role of PCDA proteins in cellular functioning.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

Allelic Analysis of the eya Gene

Fly Strains

Flies were cultured on standard cornmeal medium at 25° C. Mutant strains are listed in Lindsley et al., The Genome of Drosophila melanogaster, San Diego: Academic Press (1992). The wild-type strain normally used was Canton-S. Additional wild-type strains used to examine cell death were Urbana-S, Lausanne-S, Oregon-R, and Oregon-R-C, kindly provided by E. B. Lewis (California Institute of Technology).

Alleles of the eya Gene

Differentiation occurs in a timed manner in normal eye discs, progressing from posterior to anterior across the discs with the advance of the morphogenetic furrow.

Thus, for eye mutants, knowing when cell death occurs relative to the furrow would allow the determination of the developmental stage at which the cells die. Owing to the extreme phenotype of the $eya^1$ mutant, in which no furrow occurs, it is not possible to determine this stage. Therefore new eye alleles with less extreme eye phenotypes to place the cell death relative to the critical events in eye differentiation were generated. Additional alleles of the eye gene were isolated by screening for mutations that failed to complement the eye phenotype of $eya^1$, using techniques outlined below. Several mutants contributed by other laboratories were also determined to be eye alleles by genetic mapping and failure of complementation. Most of the newly generated alleles are lethal or semilethal when homozygous. The lethality is embryonic (N. M. B., unpublished data) and fails to complement an independently isolated embryonic lethal mutation, clift (Nüsslein-Volhard et al., Roux's Arch. Dev. Biol. 193:267–282 (1984). Flies bearing the clift allele in trans to the viable $eya^1$ allele show a severe eye phenotype. In addition, some eya alleles and interallelic combinations show reduced or absent ocelli, abnormal morphology of the adult brain, and female sterility. These results suggest that the eya gene has functions beyond its role in eye development; the eye function appears, in part, independently mutable. The gene also displays interallelic complementation.

Four eya alleles generated in other laboratories were obtained. These are $eya^1$ (Sved, supra), $eya^2$ (also $eya^{ph}$ or $eya^{pinhead}$; T McQuirre, Rutgers University), $eya^3$ (D. Mohler, University of Iowa, Iowa City), and $eya^4$ (ey-2 of Eisenberg et al., Dros. Inf. Serv. 70:266–268 (1991). Once the eya gene was mapped cytologically, other mutations in the region for complementation were tested.

This analysis revealed that T(2; 3)DTD46 has a breakpoint in the eya gene (Gelbart, Proc. Natl. Acad. Sci. USA 79:2636–2640 (1982) and that the mutation clift is allelic (Nüsslein-Volhard et al., supra).

35 new alleles were generated using ethyl methanesulfonate, X-rays, and P element hybrid dysgenesis as mutagens, as outlined below. All were isolated by failure to complement the eye phenotype of the eya$^1$ mutation. Putative alleles were recovered over a second-chromosome balancer chromosome.

The eye phenotypes of the new alleles, in trans to the viable eya$^1$ mutation, comprise a phenotypic series (FIG. 3). The mutants can be classified as: mild, in which the eyes are rough, but only slightly smaller than normal size (FIGS. 3B and 3F); intermediate, in which both eyes always form, but are rough and reduced in size (FIGS. 3C and 3G); severe, in which the eyes are rough, much reduced, and frequently absent from one or both sides of the head (FIGS. 3D and 3H); and completely and consistently eyeless, like the eya$^1$ mutant (see FIG. 10). In tangential sections of reduced and rough eyes of heteroallelic combinations, some ommatidia lack the full complement of photoreceptor cells (FIGS. 3E–3H). However, no obvious specific subset of cells is missing as allele severity increases, unlike in a mutant like sevenless (Harris et al., *J. Physiol.* 256:415–439 (1976). Even in severely reduced eyes, full complements of photoreceptor cells frequently form within individual ommatidia (FIG. 3H). These results suggest that eye mutations reduce the number of progenitor cells available for recruitment into the developing eye, rather than specifically eliminating any particular cell type(s).

Mutagenesis was as follows. Approximately 2050 spd$^9$ male flies were mutagenized with ethyl methanesulfonate (Lewis et al, *Dros. Inf. Serv.* 43:193–194 (1968) and mated to eya$^1$ virgin females, and the progeny were raised at 29° C. Of 90,000 flies screened, 12 independent alleles, eya$^{E1}$ to eya$^{E12}$, were isolated, one of which displayed temperature sensitivity. For the X-ray screen, about 1000 spd males were subjected to 4500 rads, then mated to eya$^1$ virgin females. From 57,000 total progeny screened, 16 alleles were isolated. Eight of these have cytologically visible rearrangements: eya$^{X1}$ with In(2L)26E;36–37, eya$^{X3}$ with T(2;3) 26E;86C, eya$^{X8}$ with In(2L) 26E;39, eya$^{X10}$ with T(2;3) 26E;67A, eya$^{X15}$ with T(2;3)26E;70A, eya$^{X16}$ with T(2;3) 26E;3L; heterochromatin, and eya$^{X9}$ and eya$^{X11}$ with complex breakpoints that were not determined.

Seven alleles (eya$^{P1}$ to eya$^{P7}$) were isolated in two independent screens using P element hybrid dysgenesis, after Robertson et al., *Genetics* 118:461–470 (1988). In the first screen, an Sp chromosome was used as the parental chromosome; in the second screen, the alleles were generated on an isogeneic wild-type second chromosome or on the Birmingham second chromosome. In both screens, progeny from the Birmingham 2 by P[ry$^+$Δ2–3] (99B) (Laski et al., *Cell* 44:7–19 (1986) cross were mated to virgin eya$^1$ females and screened for failure of complementation. In the first screen, one allele (eya$^{P1}$) was isolated of 200,000 F2 flies scored. In the second screen, 70,000 F2 flies were scored, and six additional alleles recovered. None of these alleles was associated with a P element at the chromosomal location of eya, analyzed by chromosomal in situ hybridization.

The eye disc phenotypes of eya alleles were studied in trans to the eya$^1$ chromosome marked with Cy. Cy was recombined onto the eya$^1$ chromosome by R. Hackett from the CyO second chromosome balancer. This was possible since the eya$^1$ mutation arose on an inversion (Sved, supra) with breakpoints on 2L similar to those of the balancer. This chromosome is referred to as Cy, eya$^1$.

Example 2

Isolation of Genomic and cDNA Clones

Of 16 X-ray-induced alleles, 6 with cytologically visible rearrangements in the polytene chromosomes of the larval salivary glands had a common breakpoint on the left arm of chromosome 2, in cytological region 26E. This location is consistent with the position of the eye gene determined by meiotic recombination, which placed both the eye phenotype (mapped for all cytologically normal alleles) and the lethality (mapped for eya$^{E4}$ and eya$^{P1}$) between dp and spd on the left arm of the second chromosome. The region was cloned in a 60 kb genomic walk, as described below. Restriction fragments were tested against eya breakpoint alleles by in situ hybridization to the salivary chromosomes and by Southern blot analysis, as described below. The chromosomal breaks of the eya mutants all fell within a 25 kb region (FIG. 6A).

Standard molecular techniques were from Sambrook et al., *Molecular Cloning*, in *A Laboratory Manual* (Cold Spring Harbor, N.Y.: Cold Spring Harbor Laboratory Press) (1989). Flies mutant for various eya alleles were mated to Canton-S, and polytene chromosomes of the larval salivary glands were dissected, stained with orcein, and analyzed for visible cytological rearrangements. A DNA probe for the 26E cytological region was obtained from Drosophila yeast artificial chromosome DY81 7, which spans into the region (kindly provided by I. Duncan, Washington University at St. Louis; Garza et al., *Science* 246:641–646 (1989). DNA was isolated from a 5 ml culture of DY817. This was digested with EcoRV and HincII, ligated, and amplified with primers to the yeast artificial chromosome vector, to generate by inverse polymerase chain reaction Drosophila DNA probes for the ends of the yeast artificial chromosome, as described by Ochman et al., *Amplification of flanking sequences by inverse PCR*, in *PCR Protocols: A Guide to Methods and Applications*, Innis, et al., eds., San Diego: Academic Press, pp 219–227 (1990). Primers used were 5'-GCGATGCTGTCGGAATGGAC-3' (SEQ ID NO:5) and 5'-GTTGGTTTAAGGCGCAAGACT-3' (SEQ ID NOS:3 and 3) for the EcoRV side, and 5'-CGAGTCGAACGCCCGATCTC-3' (SEQ ID NO:7) and 5'-AGGAGTCGCATAAGGGAGAG-3' (SEQ ID NO:8) for the HincII side. The polymerase chain reactions were run on a 1.5% low melt agarose gel, and the major bands were isolated. These were labeled by nick translation with bio-16-dUTP (ENZO Biochemicals) and used to probe Canton-S larval salivary gland chromosome squashes to determine the cytological site of hybridization. The signal was detected by the streptavidin-peroxidase complex (Detek-1-HRP Kit from ENZO Biochemicals). A 740 bp probe that hybridized in cytological region 26E was labeled by random primer reaction and used to screen a cosmid library from an isogeneic strain (kindly provided by J. Tamkun, University of California, Santa Cruz) and a Drosophila genomic phage library (Stratagene). Overlapping clones of the walk were oriented by chromosomal in situ analysis. The locations of the breakpoint fragments in the alleles were determined by DNA Southern analysis and chromosomal in situ analysis. cDNAs were identified and isolated from Drosophila head cDNA libraries (Itoh et al., *Proc. Natl. Acad. Sci. USA* 83:4081–4085 (1986); Zinsmaier et al., *J. Neurogenet.* 7:15–29 (1990)). cDNAs and genomic fragments in the region were subcloned into the pBluescript vector (Stratagene) and transformed or electroporated into XL-1 blue cells (Stratagene). Sequencing of cDNA and genomic clones was performed on cesium chloride-banded DNA preparations or minipreparations of plasmid DNA, using 5-deaza-dGTP (US Biochemicals) and making sequential primers. Sequence comparison with the EMBL and GenBank data bases was performed according to Pearson et al., *Proc. Natl. Acad. Sci. USA* 85:2444–2448 (1988) and Altschul et al., *J. Mol. Biol.* 215:403-410 (1990). Sequence analysis was performed using the GCG Sequence Analysis Software Package (Devereux et al., supra), the SAPS (statistical analysis of protein sequences) program (Brendel et al., supra), the PEST-FIND program (Rogers et al., supra; Rechsteiner, *Adv. Enzyme Reg.* 27:135-151 (1988)), and the algorithm of Eisenberg et al., *J. Mol. Biol.* 179:125-142 (1984) for potential a-helical transmembrane regions.

Two types of cDNAs were obtained from the screening of the cDNA libraries from poly(A)+RNA purified from adult heads. The cDNAs correspond to alternatively spliced products identical at the 3' end, but differing in the use of 5' exons (FIG. 6A). Both cDNA classes recognize transcripts of 3.5 kb on Northern blots of poly(A)+RNA from wild-type adult heads. Transcripts of 3.5 kb were detected on Northern blots of poly(A)+RNA isolated from third instar larval eye disc preparations using the cDNAs as probes (FIG. 6C). These transcripts were reduced in intensity in eye discs from $eya^1$ larvae. To determine whether additional alleles demonstrated transcripts of altered size, the cDNAs were used to probe poly(A)+RNA prepared from heads of eya mutants. Of 12 alleles that exhibit no cytologically visible chromosomal rearrangements, 1 allele showed an altered transcript of 4.7 kb ($eya^{x2}$). These results show that the transcripts are products of the eya gene.

Sequence comparison of the type I and II cDNAs showed that the 5'-most sequences differ, while the ~2800 bp of 3' sequence are shared. Conceptual translation of the type I cDNA, starting from the first potential initiation codon, revealed a single large open reading frame of 2280 nt (FIG. 7) (SEQ ID NO:1). The predicted protein has 760 residues, with a predicted molecular mass of 80 kd. The open reading frame of the alternatively spliced type II cDNA is 2298 bp. As a result of the alternative splicing, the proteins predicted for the two classes of cDNA differ in their extreme amino-terminal sequences (FIG. 7) (SEQ ID NOS:2 and 4).

Comparison with proteins in the GenBank and EMBL data bases revealed that the eya protein is novel. Study of the amino acid sequence suggests that the protein may be divided into two domains. The amino terminal half, corresponding roughly to amino acids 1-436 (numbers in reference to the type I cDNA class), is rich in alanine, glycine, and serine, and shows several single amino acid repeats, including a polyglutamine-rich stretch corresponding to an opa repeat (Wharton et al., *Cell* 40:55-62 (1985)). The carboxy-terminal half of the protein has fewer amino acid repeats and contains three charged stretches that are arranged as basic- acidic-basic domains, although the protein as a whole is predicted to be relatively neutral (predicted pI=6.8). In addition to these features, the protein is predicted to have five hydrophobic a-helical stretches (FIG. 7 legend; Eisenberg et al., supra). Given the nuclear localization of the gene product (below), these stretches are unlikely to represent transmembrane domains.

Example 3

Analysis of RNA and In Situ Expression

Nucleic acid was extracted using a modification of the procedure of Sargent et al., *Dev. Biol.* 114:238-246 (1986). Adult flies and embryos were collected and stored frozen at -70° C. Eye-antennal disc complexes, with mouth hooks attached, were dissected and immediately frozen on dry ice. Eye disc poly(A) RNA was prepared using the MicroFastTrack System (Invitrogen Corporation). For adult tissue, body parts ground to powder in liquid nitrogen were mixed with 4.2M guanidine isothiocyanate, 0.5% Sarkosyl, 25 mM Tris (pH 8.0), 0.7% 2-mercaptoethanol, at a ratio of 1 g of tissue per 30 ml. Samples were Dounce homogenized. Tubes were prepared with 1 vol of phenol extraction buffer (100 mM Tris [pH 8.01], 10 mM EDTA, 1% SDS) layered over 2 vol of phenolchloroform. One volume of tissue suspension was added, mixed, and centrifuged. The suspension was extracted twice more with an equal volume of phenolchloroform, then once with chloroform. The nucleic acid was precipitated with an equal volume of isopropanol.

Poly(A)+RNA was isolated over oligo(dT) columns by the FastTrack mRNA isolation protocol (Invitrogen Corporation). The RNA was then separated on 1% agarose-formaldehyde gels and blotted onto reinforced nitrocellulose paper (Schleicher & Schuell). Probes were made by random primer labeling or by making single-stranded RNA probes using the T7 and T3 promoters of the pBluescript vector. The direction of transcription determined by single-strand probes agreed with the structure of the cDNAs by sequence analysis.

The results show that a transcript of 3.5 kb that is disrupted by at least five of the breakpoint alleles; it is present in wild-type adult heads and is less abundant in heads of $eya^1$ flies (FIG. 6B). It is also present in embryos.

To study the temporal and spatial expression patterns of transcription of the gene in normal eye discs, whole-mount tissue in situ hybridization was done as follows, using a modification of the protocol of Tautz et al., *Chromosoma* 98:81-85 (1989). Probes of both type I and type II cDNAs were made by random primer labeling, using digoxigenin-11-dUTP (Boehringer Mannheim). After hybridization and detection of the signal (Boehringer Mannheim Genius Kit), discs were mounted in Aquamount (Lerner Laboratories). Some discs were postfixed 30 min in 1% glutaraldehyde, 1% paraformaldehyde in 0.1M phosphate buffer (pH 7.4), dehydrated, and embedded in Epon. Serial sections of 0.8 μm were cut, lightly stained with toluidine blue, and mounted under Permount for photography.

The results show that strong eya RNA expression occurs in the region of the disc just anterior to the furrow (FIGS. 8F and 8G). The transcript is also present posterior to the furrow, primarily in the basal region of the disc. In addition, two sites of expression are present on the edge of the eye disc, far anterior to the furrow, near the antennal disc (FIG. 8G), that probably correspond to the progenitors of the ocelli, which are derived from this area (Bryant, *Pattern formation in imaginal discs*, in *The Genetics and Biology of Drosophila*, Ashburner et al., eds. London: Academic Press, pp 229-335, (1978). The ocelli are, in fact, missing in some heteroallelic combinations of eya mutants (unpublished data).

To determine the protein expression pattern, mouse polyclonal antiserum against a fusion protein was raised as follows. A 2.3 kb SmaI fragment of type I cDNA was subcloned into the SmaI site of expression vector pGEX-2 (Smith et al., *Gene* 67:31-40 (1988). Sequence analysis confirmed that the insert was in frame. The fusion protein was of the predicted size of 86 kd, of which 60 kd corresponded to the carboxy-terminal 551 amino acids of the cDNA and 26 kd to glutathione S-transferase. The protein sequence produced is common to both types I and II cDNAs. A 500 ml culture was grown 1.5 hr at a 1:10 dilution in LB plus ampicillin, then the fusion protein was induced by addition of 1 mM isopropyl β-D-thiogalactopyranoside. The cells were collected by centrifugation at 4,000× g for 5 min, then resuspended in 7.5 ml of 50 mM Tris(pH 8.0), 1 mM EDTA, 100 mM sodium chloride, 1 mM phenylmethylsulfonyl fluoride. Lysozyme was added to 0.3 mg/ml, and the sample incubated at room temperature for 20 min. DNAase I was then added to 3 mg/ml for another 30 min. The sample was spun at 5,000× g for 10 min, and resuspended in 9 ml of 50 mM Tris(pH 8.0), 10 mM EDTA, 100 mM sodium chloride, 1 mM phenylmethylsulfonyl fluoride, 1% Triton X-100, and allowed to sit 10 min on ice. This was spun at 10,000× g for 15 min, resuspended in 4 ml of Laemmli sample buffer, and boiled. One milliliter of the sample was run on a preparative 0.1% SDS-7.5% polyacrylamide gel, stained 10 min in 0.05% Coomassie blue in water, destained, and the region of the gel with the fusion protein sliced out. Mice were immunized ten times with 50 μg of fusion protein per injection, and tail sera were collected. The antigen recognized by the polyclonal antiserum is expressed ectopically in heat-shocked transformant larvae carrying the hsp-eya minigene construct.

The pattern of antiserum staining revealed that the eya protein first becomes detectable in cells of the eye portion of the eye-antennal disc during the second larval instar; the expression is graded, being stronger in cells in the posterior and edges of the eye portion of the disc, than in cells in the anterior and central region (FIG. 8A). This staining pattern persists to the third larval instar (FIG. 8B). As the morphogenetic furrow forms, the protein stays on in a graded manner anterior to it, with strongest expression just anterior (FIGS. 8C and 8D). Protein expression persists in the cells as the furrow passes (FIGS. 8D and 8E). Posterior to the furrow, the expression is patterned, reflecting the array of developing neural clusters. Cells with nuclei in the basal region of the epithelium, which are presumably cells not yet recruited into developing neural clusters, show expression of the protein; in the apical region of the disc, expression is strong in some cells of the differentiating neural clusters (FIGS. 8D and 8E). The protein seems to be localized in the nucleus; it is not present in the nucleolus (FIG. 8E). In animals homozygous for the eya$^1$ allele, which have normal ocelli but are eyeless (see FIG. 10), eya protein expression occurs in the eye discs only in the ocellar progenitors (data not shown). The lack of detectable protein expression in the eye progenitor cells of the mutant indicates that it is null or a severe hypomorph for eya gene activity in these cells. The onset of expression of both transcript and protein in the progenitor cells anterior to the morphogenetic furrow, where the increase in cell death occurs in eya mutants, is consistent with critical functioning of the gene in events that precede furrow formation.

We also examined the expression pattern of the eya gene elsewhere in normal animals (unpublished data). This analysis revealed a specific and dynamic expression pattern in the embryo, beginning with the onset of zygotic gene expression in the cellular blastoderm, and continuing in regions of the developing head and in segments. The gene does not appear to be expressed in the embryonic eye primordia or in eye discs during the first larval instar. In addition, the eya gene is expressed in select other tissues in patterns that may be related to the embryonic lethal and adult phenotypes of select eya alleles. Thus, far from being ubiquitously expressed, the eya gene shows select expression in specific regions of the developing and adult organism.

Example 3

Histology and Immunocytochemical Analysis

The apparent arrest in development of the eye disc epithelium in eya$^1$ animals could result from a block in cell division preventing the generation of progenitor cells. Alternatively, the cells might be generated but could fail to differentiate normally. To distinguish between these possibilities, mutant and wild-type larvae were labeled in vivo with pulses of 5-bromodeoxyuridine (BrdU). BrdU is incorporated into the DNA of dividing cells in S phase; these cells can then be visualized by immunofluorescence using antibodies specific for BrdU (Truman et al., *Dev. Biol.* 125:145–157 (1988). In normal eye discs, dividing cells were labeled in a scattered pattern in the region anterior to the furrow where progenitor cells are generated. At the furrow, DNA synthesis was absent. Posterior to the furrow, cell division resumed in a restricted band, reflecting pattern formation events (Ready et al., supra). In eya$^1$ mutant eye discs at the early third instar larval stage, the amount of cell division was similar to that in the region anterior to the furrow in normal eye discs of the same stage (data not shown). This result suggests that cells in the eya$^1$ eye disc do divide; a lack of cell division to generate progenitor cells seems not to be the primary defect.

Given that progenitor cells divide in the eya$^1$ eye disc, the possibility that a lack of normal differentiation results from the loss of cells by death was examined. In normal third instar larval eye discs relatively little cell death is present (see FIG. 4E). In contrast, eye discs of eya$^1$ animals reveal a dramatic increase in cell death during the third instar larval stage. Cells are present in the eya$^1$ eye disc that appear condensed and refractile by light microscopy, reminiscent of cells dying by programmed cell death in C. elegans (see FIG. 4D; Sulston et al., *Dev. Biol.* 56:110–156 (1977)). Dead cellular material also fluoresces brightly when stained with acridine orange (Spreij, supra). Such staining reveals a great increase in the number of dead cells in eye discs of the eya$^1$ mutant (see FIG. 4H). In the electron microscope, eya$^1$ mutant eye discs show electron dense condensed fragments of cells and many examples of these fragments engulfed within other cells (see Figures). These morphological features are characteristic of cells dying by programmed cell death (Wyllie et al., *Int. Rev. Cytol.* 68:251–306 (1980); Kerr et al., Apoptosis, in *Perspectives on Mammalian Cell Death*, Pollen, ed. (Oxford: Oxford University Press), pp 93–128 (1987); Clarke, *Anat. Embryol.* 181:195–213 1990). These results suggest that the defect in the eya$^1$ mutant is a loss by cell death of eye progenitor cells.

Scanning electron microscopy was performed on unfixed flies and on flies stored in 70% ethanol, dehydrated to 100% ethanol, and critical point dried. In both cases, flies were coated with gold-palladium 80:20. For tangential eye sections, fly heads were fixed in 1% glutaraldehyde, 1% paraformaldehyde in 0.1M phosphate buffer (pH 7.4), dehydrated, and embedded in Epon (Polysciences, Inc.). Sections of 0.7 μm thickness were cut, lightly stained with 1% toluidine blue, 1% borax solution in water, and mounted in Permount (Fisher Scientific). To examine eye discs by transmission electron microscopy, discs were dissected in 0.1M phosphate buffer (pH 7.4), fixed for 1 hr in 1% glutaraldehyde, 1% paraformaldehyde in 0.1M phosphate buffer (pH 7.4). Tissue was stained 1 hr in 1% osmium, 0.5% uranyl acetate, dehydrated through ethanol, and embedded in Epon, and serial 0.08 μm sections were cut.

Silver staining of adult heads was performed according to the procedure of Meyerowitz et al., supra, as modified by Harte et al., *Genetics* 101:447–501 (1982) and K. Stark (Yale University), who kindly shared many helpful suggestions. Labeling and detection of cells in S phase in wild-type and eya$^1$ mutant eye discs was performed as described by Truman et al., supra, with the following modifications.

Staged larvae were labeled in vivo for 2 hr with BrdU at 1 mg/ml. Primary anti-BrdU antibody (Becton-Dickinson) incubation was overnight at 4° C. with slow shaking, and the secondary antibody was fluorescein conjugated (Cappel Laboratories).

Eye discs were stained with acridine orange according to the protocol of Spreij, supra. Dead cellular material fluoresces brightly when stained with acridine orange. After dissection in Ringer's solution, discs were incubated 5 min in $1.6 \times 10^{-6}$ M acridine orange in Ringer's solution, rinsed, and viewed with fluorescence optics.

Eye discs were dissected, fixed, and stained with MAb 22C10 overnight, as described by Van Vactor et al., *Cell* 67:1145–1155 (1991), with some modifications. The horse-radish peroxidase-conjugated secondary antibody (Bio-Rad Laboratories) was used at a 1:50 dilution, and substrate was detected with 0.5 mg/ml diaminobenzidine plus 2 mg/ml NiCl. For visualization of the eya protein with the polyclonal antisera on whole-mount preparations of eye discs, a modification of the protocol of Renfranz et al., supra, was used. Eye discs were dissected in tris-buffered saline (100 mM Tris [pH 7.5], 130 mM NaCl, 5 mM KCl, 5 mM NAN$_3$, 1 mM EGTA), fixed 30 min in 2% paraformaldehyde in tris-buffered saline, then permeabilized 30 min in 0.5% Nonidet P-40 in tris-buffered saline. After rinsing in tris-buffered saline, discs were incubated 30–60 min in tris-buffered saline plus 5% normal goat serum (Vector Laboratories). Primary antibody staining was at 1:500–1:1000 in tris-buffered saline plus 5% normal goat serum for 60 min, discs were rinsed 30 min in tris-buffered saline plus 5% normal goat serum, then incubated in fluorescein-conjugated secondary antibody at 1:500 (Cappel) diluted in tris-buffered saline plus 5% normal goat serum. After washing 30 min in tris-buffered saline plus 5% normal goat serum, discs were mounted in 90% glycerol plus 0.1% phenylene, diamine, and viewed by fluorescence microscopy. Localization by light microscopy of the eya protein with the mouse polyclonal antiserum was by the protocol above for MAb 22C10, with some modifications. The antiserum was used at a 1:500 dilution. Following substrate detection, discs were postfixed 20 min in 1% paraformaldehyde plus 1% glutaraldehyde in 0.1M phosphate buffer (pH 7.4), and embedded in Epon. Longitudinal sections of 0.7 μm thickness were cut, and tissue was lightly stained with 1% toluidine blue, 1% borax solution in water, prior to mounting in Permount.

Eya mutants with reduced adult eyes exhibit neural differentiation in the eye disc, as illustrated by staining with MAb 22C10 (FIGS. 4A–4D). However, consistent with reduced eyes in the adult, fewer neural clusters form in the eye mutant larval eye disc. With increasing severity of the phenotype, the number of clusters that form decreases. In eye discs of larvae expressing intermediate and severe allele combinations, where very reduced numbers of ommatidia form, the clusters develop in the posterior-most region of the eye disc (FIGS. 4C and 4D). When examined with BrdU labeling, eye discs of larvae expressing intermediate allele combinations show cell division both anterior to the furrow and in a band posterior to the furrow, reflecting aspects of pattern formation seen in normal eye discs (data not shown). ID eyeless allelic combinations, no furrow is seen, no clusters differentiate, and dramatic increases in cell death occur in the eye discs, as in the eya$^1$ mutant. Staining for dead cellular material revealed a great increase in the number of dead cells in eye discs of the eya$^1$ mutant (see FIG. 4H). In the electron microscope, eya$^1$ mutant eye discs show electron dense condensed fragments of cells and many examples of these fragments engulfed within other cells (see FIG. 5). These morphological features are characteristic of cells dying by programmed cell death, rather than necrosis, since necrotic cells swell, losing membrane activity. (Wyllie et al., supra; Kerr et al., supra; Clarke, supra.) In contrast, dying cells in eya mutant discs appear to condense, becoming refractile by light microscopy. By transmission electron microscopy, condensed bodies containing intact cellular organelles are seen; some bodies are engulfed within healthy cells, as is typical of programmed cell death in other systems where the debris is rapidly removed by phagocytosis.

Cell death in the mutant discs overlaps a stage during which some progenitor cell death normally occurs prior to furrow formation in eye morphogenesis (see FIG. 4E; Spreij, supra; Wolff et al., supra). This suggests that loss of eya activity skews the distribution of cells into a normally occurring cell death pathway. In eye discs of larvae bearing mild to severe alleles, only a fraction of the progenitor cells undergoes cell death; the remaining cells appear to proceed normally to form a furrow with clusters differentiating behind it. The incidence of cell death anterior to the furrow appears to correlate inversely with the final number of ommatidia. Since mutation of the eya gene does not seem to affect division of the progenitor cells, the data are consistent with lack of eya activity resulting in a switch in cell fate from the pathway of differentiation to that of cell death. Moreover, the increased cell death in the mutant discs appears highly restricted to the region anterior to the furrow: dying cells are not observed within the furrow, and no increase in cell death is seen posterior to it. These observations suggest the existence of a regulated mechanism, acting prior to furrow formation, that allows some cells rather than others to undergo pattern formation events. The data suggest that a selection point may normally occur prior to furrow formation when some cells, presumably inappropriate or extraneous, are eliminated; the eya gene appears to function critically in this selection process.

In addition, the result that the eye disc of the eya$^1$ mutant closely resembles that of the eya$^1$ allele in trans to lethal alleles, is consistent with the eya$^1$ mutant being a severe hypomorph or null for a necessary eye function of the eye gene.

Since the eye discs of mutants showing partial eye development display a quasi-normal framework of differentiation, the cell death relative to the morphogenetic furrow can be placed. Examination of eye discs of such eye mutant combinations revealed dramatic increases in cell death restricted to the region anterior to the furrow (FIGS. 4E–4H; FIG. 5). This could be observed by differential interference contrast optics, in which dead cells appear condensed and refractile (FIGS. 4C and 4D), and highlighted by fluorescence microscopy with acridine orange (FIGS. 4E–4H). In several different wild-type strains of D. melanogaster examined, we consistently find some degree of cell death just anterior to the furrow, varying from a small amount to a thin band, as in FIG. 4E (also Spreij, supra; Wolff et al., supra). In eye discs from eya allelic combinations that form mildly reduced eyes, the increase in cell death also occurs as a band just anterior to the furrow, in the same region where the low level of cell death normally takes place (compare FIG. 4E with 4F). This suggests that loss of eye function may shunt cells into a normally occurring cell death pathway anterior to the furrow. In eye discs from intermediate and severe allele combinations, which form more severely reduced eyes, the amount of cell death is greater, covering a broader region anterior to the furrow (FIGS. 4G and 4H). Normal discs also show some cell death in the differentiating region of the disc posterior to the furrow during the third instar (Spreij, supra; Wolff et al., supra); this cell death is not increased by eya mutations (FIGS. 4E–4H).

The ultrastructure of the dying cells in the region anterior to the furrow was examined by transmission electron microscopy. In both normal (data not shown) and mutant discs (FIG. 5), the morphological changes appear characteristic of programmed cell death (Wyllie et al., supra; Kerr et al., supra; Clarke, supra.) Dead cells condense into electron-dense bodies containing well-preserved cellular organelles. These bodies seem to be engulfed by surrounding cells, so that the debris is cleared by the time the furrow passes. Consistent with observations using acridine orange, the elevated level of cell death is restricted to the region of the disc anterior to the furrow (FIG. 5A). In eye discs of larvae bearing mild allele combinations, the cell death is rapid: since the furrow advances at a rate of about 1 column of clusters per 2 hr, it was estimated that dead cells fragment and are cleared within 2–4 hr.

The earliest defect observed in mutant discs is an increase in the number of cells undergoing cell death before furrow formation. No obvious morphological or structural abnormalities in progenitor cells anterior to the furrow, other than changes characteristic of programmed cell death in dying cells, could be found by transmission electron microscopy. Furthermore, in alleles that make reduced eyes, progenitor cells that survive anterior to the furrow appear to enter into the normal progression of events marked by the furrow. Together, these results suggest that the primary phenotype of loss of eye gene function in the eye is the loss of progenitor cells through programmed cell death prior to furrow formation.

Example 4

Transformation Rescue

To show definitively that the biological activity of the eya gene is encoded in the transcripts identified, transformation rescue of the eyeless phenotype was done. Type I cDNA was subcloned into the pHT4 vector (Schneuwly et al., Nature 325:816–818 (1987)), downstream of the Drosophila hsp70 heat shock promoter, and injected into embryos, as outlined below. Stable inserts were crossed into eya$^1$ and eya$^2$ mutant flies, which express viable eyeless phenotypes. Mutant larvae, harboring an hsp-eya minigene insert, were heat pulsed for 1 hr every 6–8 hr, from the first instar larval stage to pupation, to determine whether expression of the normal cDNA could restore eye development. Type I cDNA was subcloned into the KpnI site of the vector pHT4 (Schneuwly et al., supra), to make an hsp-eya minigene for transformation. The cDNA was first subcloned into the EcoR1 site of a modified pBluescript vector with a KpnI linker added to the SmaI site (Van Vactor et al., supra). Partial digests were used, since the cDNAs have an internal KpnI site. The pHT4 vector contains the Drosophila hsp70 promoter, a polyadenylation site from SV40, and ry$^+$ gene as an eye color marker. The plasmid for transformation was cesium chloride-banded, then mixed at a 5:1 ratio with a transposase source, phs$\pi$ (Steller et al., EMBO J. 4:3765–3772 (1985)). This was injected into eggs (Rubin et al., Science 218:348–353 (1982)). Lines were established from adults harboring an hsp-eya minigene insert, as assessed by eye color, then crossed into eya mutant backgrounds. Two independent transformant lines, A23.4 and A67.1, were used for rescue of the eye phenotype. To express the cDNA during development, eggs were laid in vials, then after 24 hr, heat pulsed in a 37° C. water bath for 1 hr every 6–8 hr during larval development, which was slowed to a period of about 7 days. For staged larvae, eggs were collected over 3 hr intervals, and larvae were collected within 5 hr of the second or third instar larval molts. Larvae were transferred to 0.5 ml tubes with cornmeal medium and were heat pulsed in a polymerase chain reaction machine for 30 min every 6 hr for the desired number of pulses. For heat shocks during the pupal stage, white prepupae were collected every 1–2 hr over a 9 hr period from ry$^{506}$ and transformant lines A67.1 and B58.1 in a background. Pupae were aged 15–24 hr, then heat shocked for 30 min every 6 hr for 48 hr. Although this treatment caused much death of both control and experimental animals, eyes could be scored on emerged flies and with dissection on dead pupae. The period of heat shock covered the phase of pigment cell death, which normally occurs 35–50 hr after pupation (Wolff et al., supra).

The results show that mutant lines bearing the minigene and raised without heat shock were eyeless (FIG. 9B). Heat pulsing eya$^1$ and eya$^2$ mutant larvae lacking an insert had no effect on the mutant phenotype. However, heat pulsing of eya$^1$ and eya$^2$ mutant larvae with an hsp-eya minigene insertion restored the adult compound eye (FIG. 9C). Tangential sections through rescued eyes showed that the restored ommatidia appear normal (FIG. 9E). No discernible dominant effects of heat shock-induced expression of the hsp-eya minigene were evident in normal flies or in eya mutants, other than rescue of the eye in the latter.

The effective period of heat shock- induced rescue of the eya mutant phenotype was defined by heat pulsing during the second and third instar larval stages. Heat pulses during only the second instar larval stage were ineffective. However, eyes of small size could be restored with three 30 min heat pulses every 6 hr starting from the third instar larval molt (data not shown), the stage during which the morphogenetic furrow begins. With four or five heat pulses, eyes of intermediate size could be restored, and, additionally, were restored to a greater percentage of transformants. These data suggest that eya activity is required during the stage of development at which some cell death normally occurs anterior to the furrow.

Rescue of the eya mutant phenotype with the heat shock cDNA construct shows that the protein encoded by the type I cDNA can provide the biological activity required to rescue the progenitor cells from death and restore the sequence of patterning events that generate an eye.

What is claimed is:

1. A recombinant nucleic acid comprising DNA having the sequence shown in FIG. 7 (SEQ ID NO:1 or 3).

2. An expression vector comprising transcriptional and translational regulatory DNA operably linked to DNA comprising the sequence shown in FIG. 7 (SEQ ID NO:1 or 3).

3. A host cell transformed with an expression vector comprising a nucleic acid comprising the sequence shown in FIG. 7 (SEQ ID NO:1 or 3).

4. A host cell transformed with an expression vector according to claim 2.

5. A method of producing a programmed cell death antagonist protein comprising:

a) culturing a host cell transformed with an expression vector comprising a nucleic acid comprising the sequence shown in FIG. 7 (SEQ ID NO:1 or 3); and b) causing expression of said nucleic acid to produce a recombinant programmed cell death antagonist protein.

* * * * *